US012642488B2

(12) United States Patent
Pushpala et al.

(10) Patent No.: US 12,642,488 B2
(45) Date of Patent: \*Jun. 2, 2026

(54) ON-BODY MICROSENSOR FOR BIOMONITORING

(71) Applicant: One Health Biosensing Inc., New York, NY (US)

(72) Inventors: Ashwin Pushpala, San Francisco, CA (US); Matthew Chapman, Oakland, CA (US); Alan Szmodis, San Francisco, CA (US)

(73) Assignee: One Health Biosensing Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/405,937

(22) Filed: Jan. 5, 2024

(65) Prior Publication Data

US 2025/0009300 A1 Jan. 9, 2025

Related U.S. Application Data

(63) Continuation of application No. 17/589,475, filed on Jan. 31, 2022, now Pat. No. 11,903,738, which is a (Continued)

(51) Int. Cl.
*A61B 5/05* (2021.01)
*A61B 5/00* (2006.01)
(Continued)

(52) U.S. Cl.
CPC .......... *A61B 5/685* (2013.01); *A61B 5/14503* (2013.01); *A61B 5/14514* (2013.01); *A61B 5/14532* (2013.01); *A61B 5/14546* (2013.01);

*A61B 5/14865* (2013.01); *A61B 5/150022* (2013.01); *A61B 5/150282* (2013.01); *A61B 5/150427* (2013.01); *A61B 5/150969* (2013.01); *A61B 5/150984* (2013.01);
(Continued)

(58) Field of Classification Search
None
See application file for complete search history.

(56) References Cited

U.S. PATENT DOCUMENTS 7,120,483 B2 * 10/2006 Russell ............ A61B 5/150358
600/347
2006/0264716 A1 * 11/2006 Zander ............... A61B 5/14865
29/854
(Continued)

*Primary Examiner* — Michael R Bloch
(74) *Attorney, Agent, or Firm* — Perkins Coie LLP

(57) ABSTRACT

A microsensor and method of manufacture for a microsensor, comprising an array of filaments, wherein each filament of the array of filaments comprises a substrate and a conductive layer coupled to the substrate and configured to facilitate analyte detection. Each filament of the array of filaments can further comprise an insulating layer configured to isolate regions defined by the conductive layer for analyte detection, a sensing layer coupled to the conductive layer, configured to enable transduction, and a selective coating coupled to the sensing layer, configured to facilitate detection of specific target analytes/ions. The microsensor facilitates detection of at least one analyte present in a body fluid of a user interfacing with the microsensor.

18 Claims, 21 Drawing Sheets

Related U.S. Application Data continuation of application No. 16/942,645, filed on Jul. 29, 2020, now Pat. No. 11,272,885, which is a continuation of application No. 15/410,569, filed on Jan. 19, 2017, now Pat. No. 10,820,860, which is a continuation-in-part of application No. 14/876,692, filed on Oct. 6, 2015, now Pat. No. 10,549,080, which is a continuation of application No. 14/211,404, filed on Mar. 14, 2014, now Pat. No. 9,182,368.

(60) Provisional application No. 62/280,289, filed on Jan. 19, 2016, provisional application No. 61/905,583, filed on Nov. 18, 2013, provisional application No. 61/781,754, filed on Mar. 14, 2013.

(51) Int. Cl.

| | |
|---|---|
| *A61B 5/145* | (2006.01) |
| *A61B 5/1486* | (2006.01) |
| *A61B 5/15* | (2006.01) |
| *A61M 37/00* | (2006.01) |
| *G01N 27/327* | (2006.01) |
| *G01N 33/50* | (2006.01) |

(52) U.S. Cl.
CPC .......... *A61B 5/4839* (2013.01); *A61B 5/6849* (2013.01); *A61M 37/0015* (2013.01); *G01N 27/3271* (2013.01); *G01N 33/50* (2013.01); *A61B 2562/0209* (2013.01); *A61B 2562/028* (2013.01); *A61B 2562/046* (2013.01); *A61B 2562/12* (2013.01); *A61B 2562/125* (2013.01); *A61B 2562/182* (2013.01); *A61M 2037/0023* (2013.01); *A61M 2037/0046* (2013.01); *A61M 2037/0053* (2013.01); *A61M 2037/0061* (2013.01); *Y10T 29/49117* (2015.01)

(56) References Cited

U.S. PATENT DOCUMENTS

| | | | | |
|---|---|---|---|---|
| 2009/0099427 A1* | 4/2009 | Jina | ....................... | A61B 5/685 |
| | | | | 600/309 |
| 2010/0152651 A1* | 6/2010 | Boyden | ............... | C07K 16/283 |
| | | | | 604/113 |
| 2012/0041337 A1* | 2/2012 | Ferguson | ............... | B29C 45/37 |
| | | | | 600/573 |

* cited by examiner

130

140

150

160

170

120

150

130    130    160

140    170    150

120b

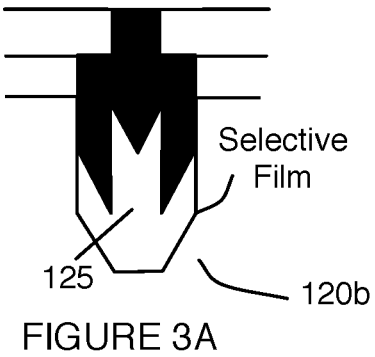
Selective
Film
125          120b
FIGURE 3A
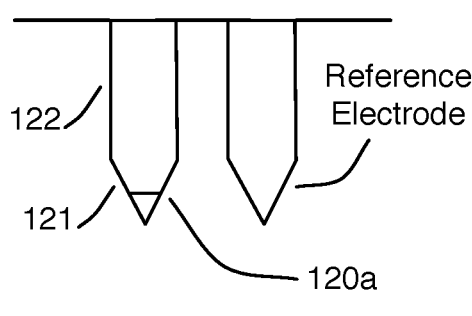
122          Reference
             Electrode
121
120a
FIGURE 3B
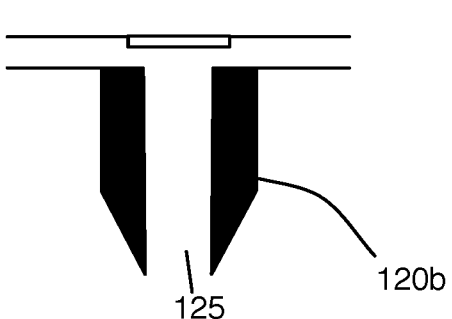
120b
125
FIGURE 3C
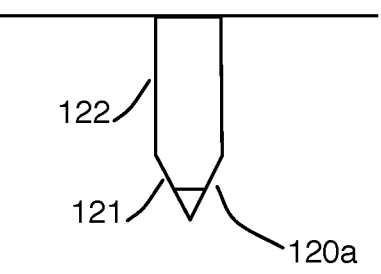
122
121
120a
FIGURE 3D
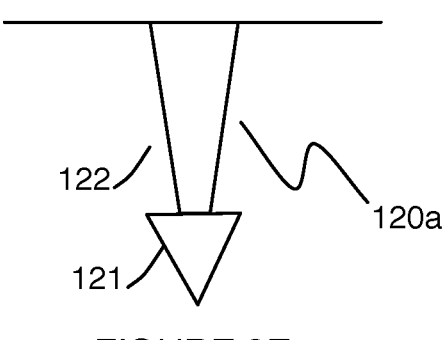
122          120a
121
FIGURE 3E
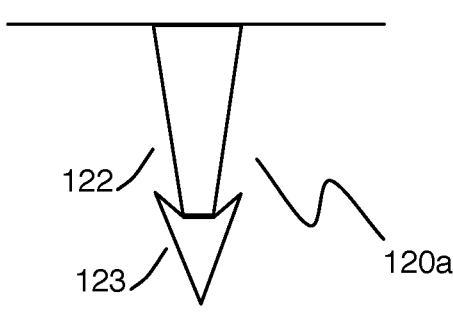
122          120a
123
FIGURE 3F
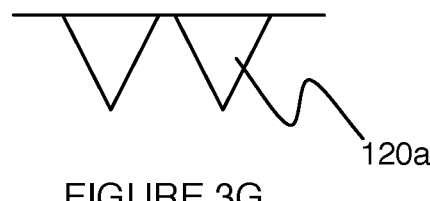
120a
FIGURE 3G
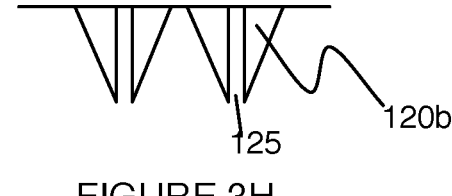
125          120b
FIGURE 3H

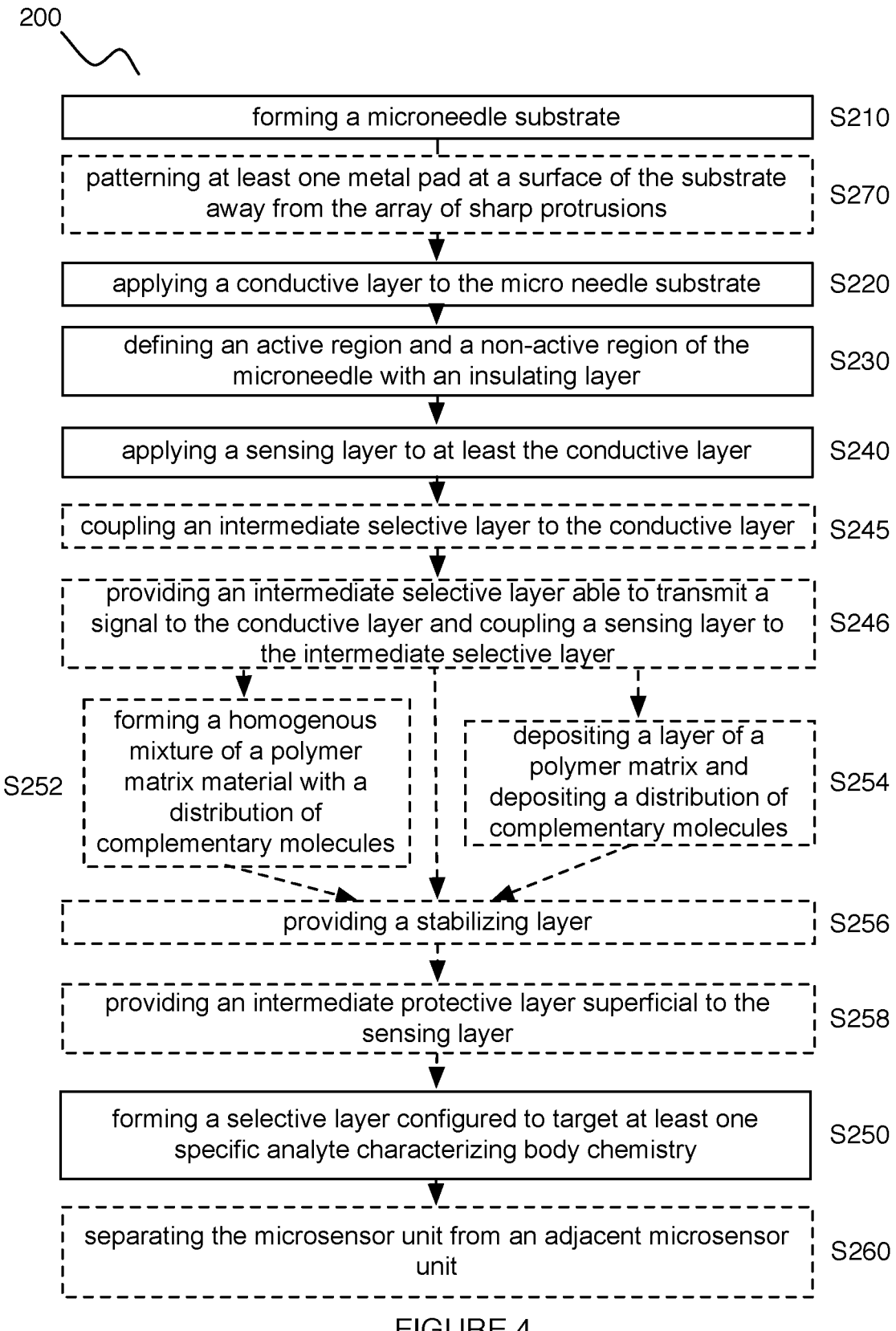

200

| forming a microneedle substrate | S210 | patterning at least one metal pad at a surface of the substrate away from the array of sharp protrusions — S270

| applying a conductive layer to the micro needle substrate | S220 |

| defining an active region and a non-active region of the microneedle with an insulating layer | S230 |

| applying a sensing layer to at least the conductive layer | S240 | coupling an intermediate selective layer to the conductive layer — S245 providing an intermediate selective layer able to transmit a signal to the conductive layer and coupling a sensing layer to the intermediate selective layer — S246

S252 — forming a homogenous mixture of a polymer matrix material with a distribution of complementary molecules depositing a layer of a polymer matrix and depositing a distribution of complementary molecules — S254 providing a stabilizing layer — S256 providing an intermediate protective layer superficial to the sensing layer — S258

| forming a selective layer configured to target at least one specific analyte characterizing body chemistry | S250 | separating the microsensor unit from an adjacent microsensor unit — S260

FIGURE 4

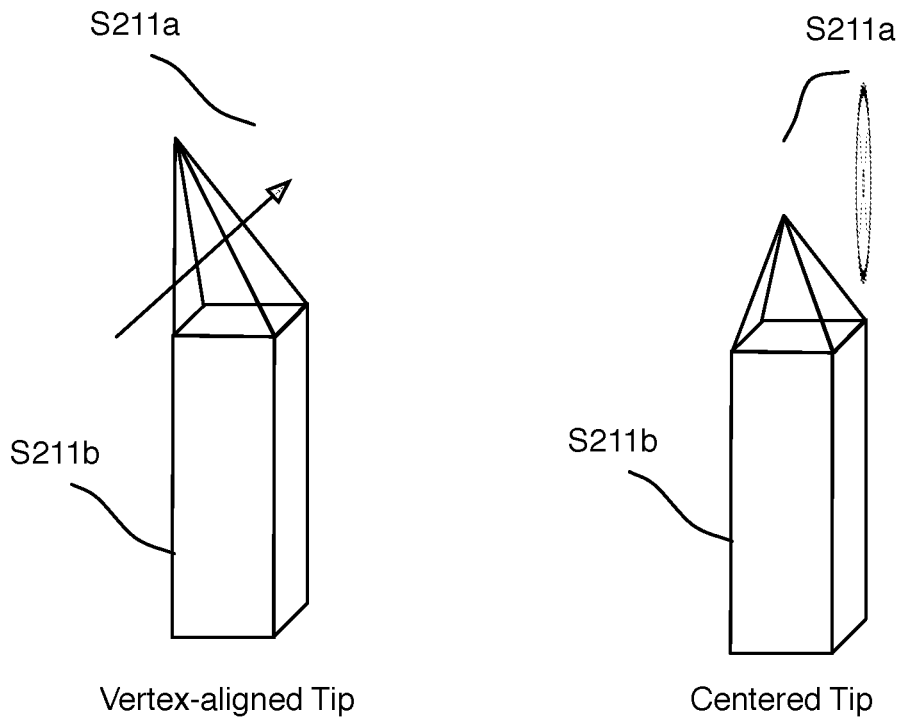
S211a
S211b
Vertex-aligned Tip
S211a
S211b
Centered Tip
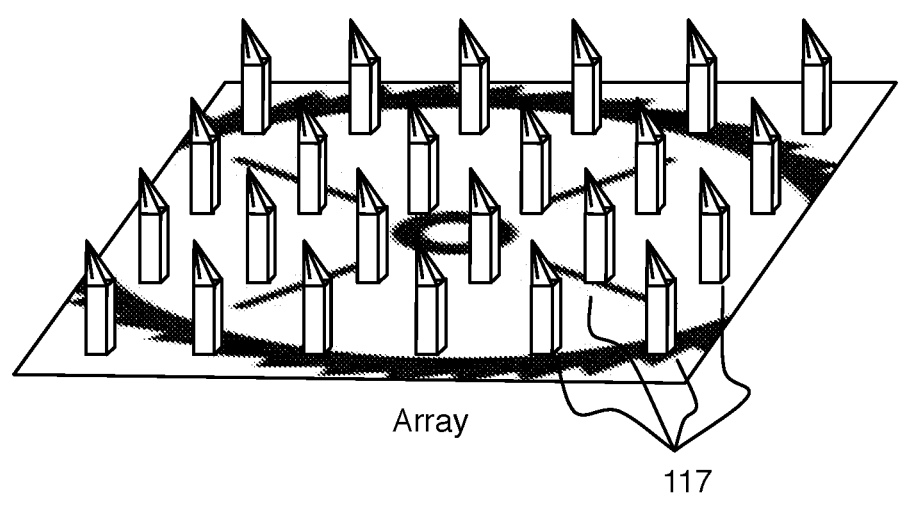
Array
117
FIGURE 5C

S210

S210'

S210

S220

S230

S283

Remove Back-Side
Insulation

Anisotropically Remove
Front-Side Insulation

Remove Sacrificial Layer

S242

Cross Section View                    Unit Cell View orthogonal dicing
cuts to create
array of
protrusions in
substrate Cross Section View                    Unit Cell View generate partial
vias with first set
of cuts through top
side to first depth complete vias
with second set
of cuts through
bottom side to
second depth,
orthogonal to
first set of cuts Cross Section View                    Unit Cell View form first insulating layer form first conductive layer form second insulating layer form second conductive layer
...

pattern back side
to form first
electrode contact

Cross Section View                    Unit Cell View form additional
electrode contacts form sharp tips Cross Section View                    Unit Cell View Metallize conductive
surfaces to form
electrodes and
contacts Separate adjacent
sensor units Cross Section View                    Unit Cell View Form protective layer
(e.g., oxide)

Cross Section View                    Unit Cell View

Pattern and etch frontside protective layer

Pattern and etch backside protective layer

Cross Section View                    Unit Cell View

Timed etch to form vias through substrate

Remove remaining protective layer

ON-BODY MICROSENSOR FOR BIOMONITORING

CROSS-REFERENCE TO RELATED APPLICATIONS

This application is a continuation of U.S. application Ser. No. 17/589,475, filed Jan. 31, 2022, which is a continuation of U.S. application Ser. No. 16/942,645, filed Jul. 29, 2020 (U.S. Pat. No. 11,272,885), which is a continuation of U.S. application Ser. No. 15/410,569, filed Jan. 19, 2017 (U.S. Pat. No. 10,820,860), which is a continuation-in-part of U.S. application Ser. No. 14/876,692, filed Oct. 6, 2015 (U.S. Pat. No. 10,549,080), which is a continuation of U.S. application Ser. No. 14/211,404, filed Mar. 14, 2014 (U.S. Pat. No. 9,182,368), which claims priority to U.S. Provisional Application No. 61/905,583, filed Nov. 18, 2013 and claims benefit of U.S. Provisional Application No. 61/781,754, filed Mar. 14, 2013. U.S. application Ser. No. 15/410,569, claims priority to U.S. Provisional Application No. 62/280,289, filed Jan. 19, 2016. All aforementioned applications and patents are incorporated herein by reference in their entireties.

TECHNICAL FIELD

This invention relates generally to the medical device field, and more specifically to a new and useful on-body microsensor for biomonitoring.

BACKGROUND

Biomonitoring devices are commonly used, particularly by health-conscious individuals and individuals diagnosed with ailments, to monitor body chemistry. Conventional biomonitoring devices typically include analysis and display elements. Such biomonitoring devices perform the tasks of determining one or more vital signs characterizing a physiological state of a user, and provide information regarding the user's physiological state to the user. In variations, biomonitoring devices can determine an analyte level present in a user's body, and provide information regarding the analyte level to the user; however, these current biomonitoring devices typically convey information to users that is limited in detail, intermittent, and prompted by the command of the user. Such biomonitoring devices, including blood glucose meters, are also inappropriate for many applications outside of intermittent use, due to design and manufacture considerations. Additionally current devices are configured to analyze one or a limited number of analytes contributing to overall body chemistry, due to limitations of sensors used in current biomonitoring devices.

There is thus a need in the medical device field to create a new and useful on-body microsensor for biomonitoring. This invention provides such a new and useful microsensor.

BRIEF DESCRIPTION OF THE FIGURES

FIGS. 3A-3H depict embodiments of filament geometries;

FIG. 4 depicts an embodiment of a manufacturing method for an on-body microsensor for biomonitoring;

FIGS. 5A-5C depict embodiments of a portion of a manufacturing method for an on-body microsensor for biomonitoring;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Microsensor

Figures 1A, 1B:
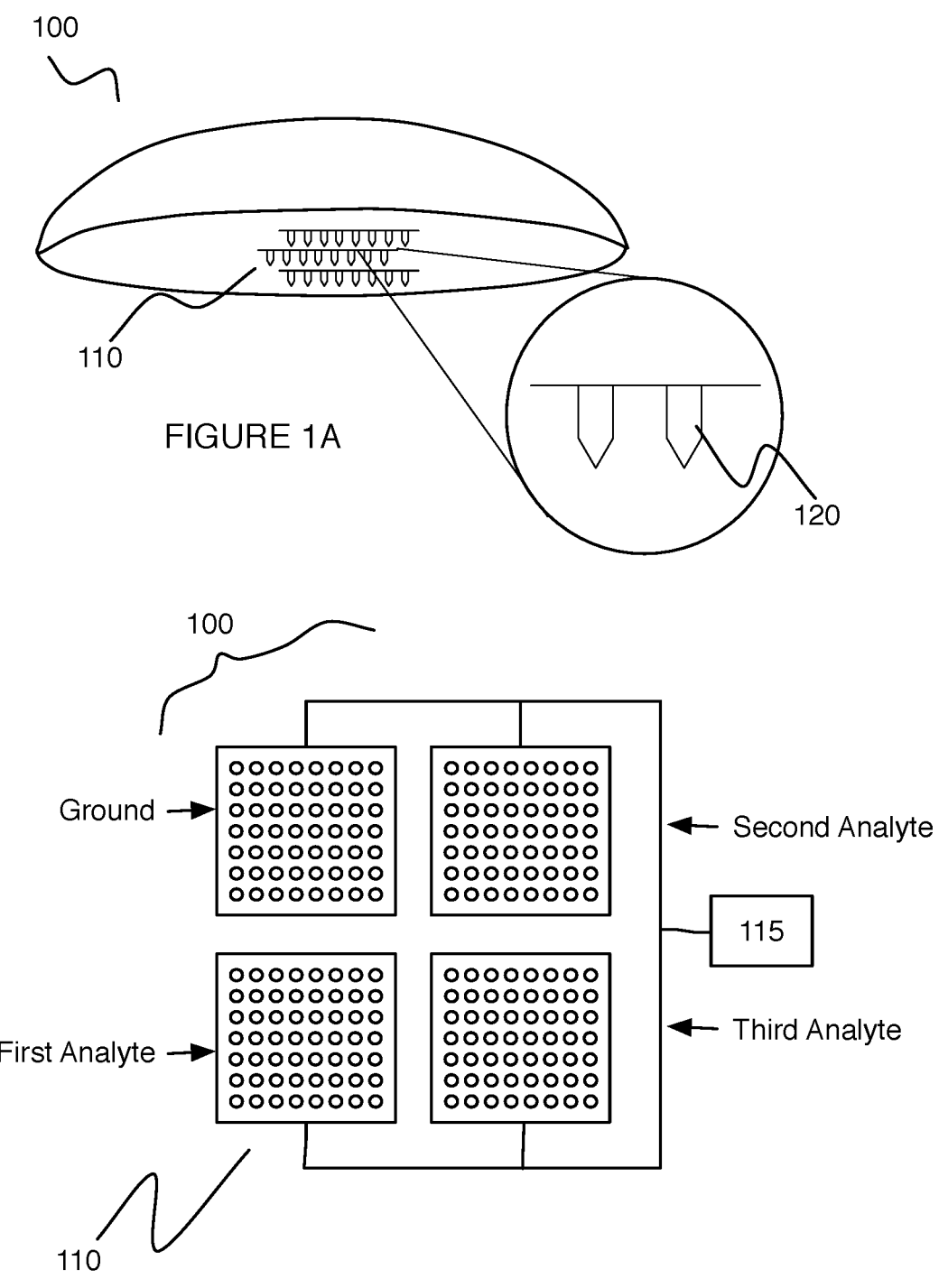
FIG. 1A depicts an embodiment of a microsensor for biomonitoring.
FIG. 1B depicts an embodiment of an array of filaments, and a microsensor coupled to an electronics module.
Figure 2A:
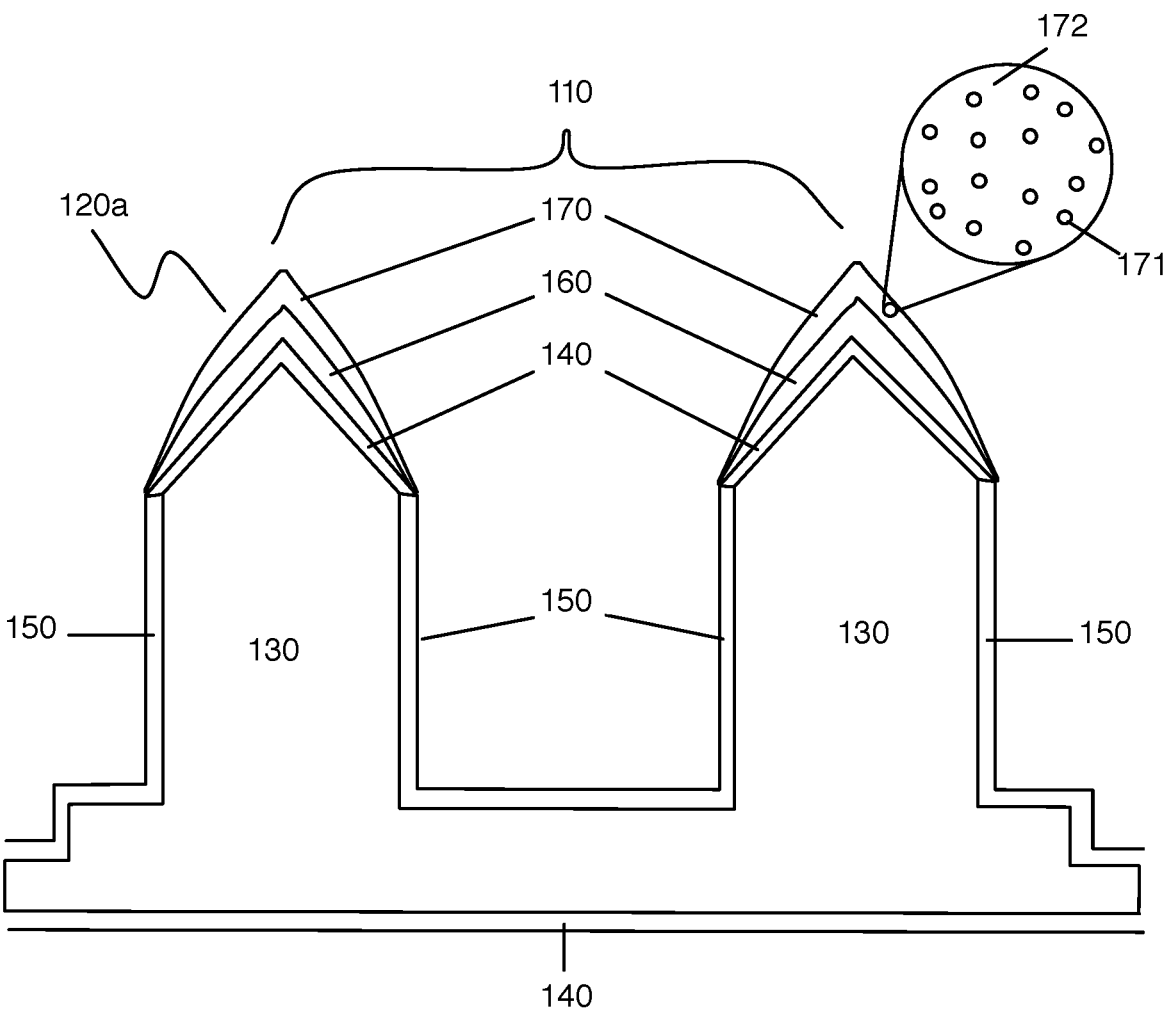
FIG. 2A depicts an embodiment of a filament for biomonitoring.
Figure 2B:
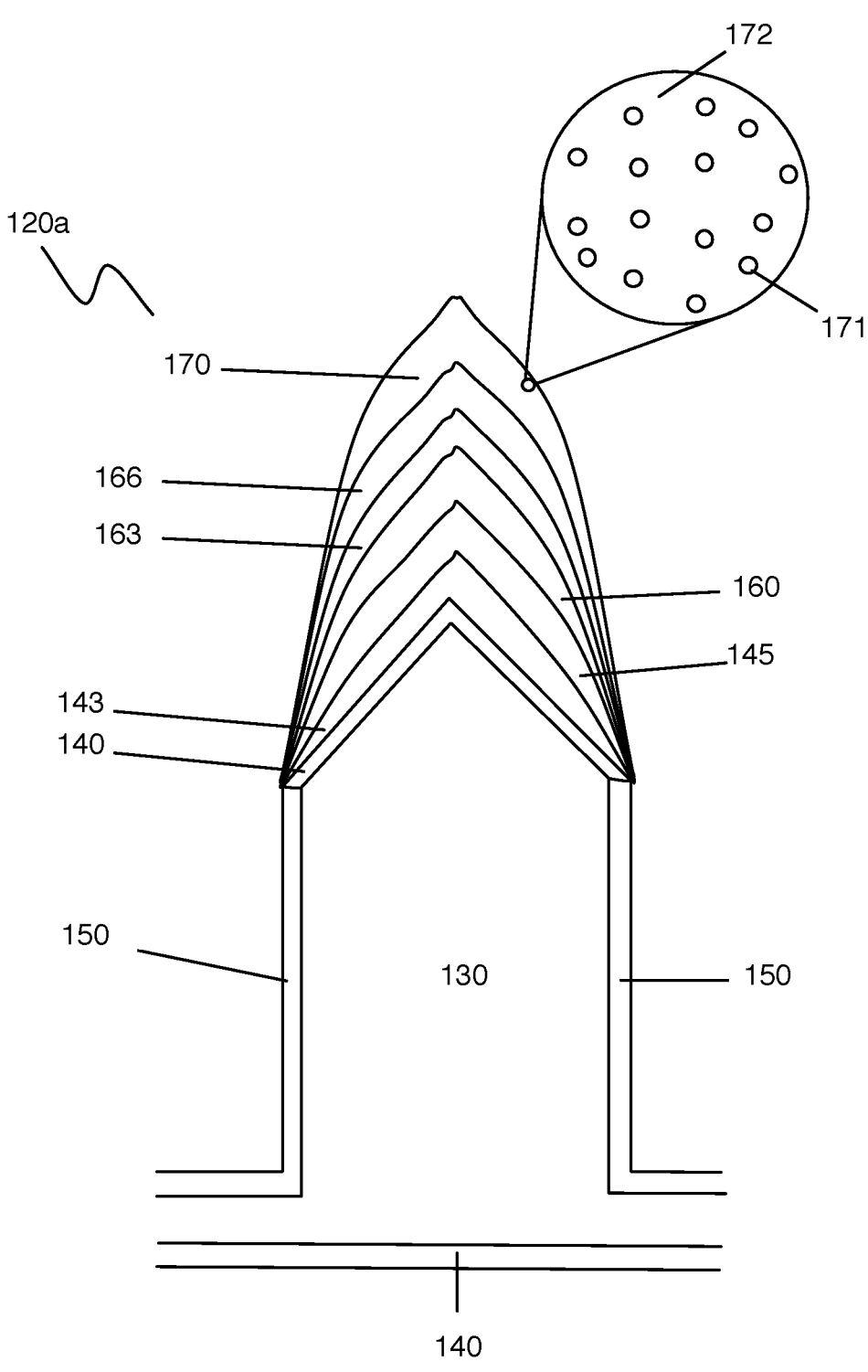
FIG. 2B depicts another embodiment of a filament for biomonitoring.

As shown in FIGS. 1A, 2A, and 2B, an embodiment of a microsensor 100 comprises an array of filaments 110, wherein each filament 120 of the array of filaments 110 comprises a substrate 130 and a conductive layer 140 configured to facilitate analyte detection. Alternatively, the substrate 130 itself can be conductive with no additional conductive layer 140. Each filament 120 of the array of filaments 110 can further comprise an insulating layer 150 configured to isolate regions for analyte detection, a sensing layer 160 configured to enable transduction of an ionic concentration to an electronic voltage, and a selective coating 170 configured to facilitate detection of specific target analytes/ions. Any filament 120 of the array of filaments 110 can further comprise an adhesion coating 180 configured to maintain contact between layers, coatings, and/or substrates of the filament 120, and a temporary functional layer 190 configured to facilitate penetration of a filament into the body. The microsensor 100 and the array of filaments 110 thus function to penetrate a user's skin in order to sense at least one target analyte characterizing the user's body chemistry. Preferably, the microsensor 100 is configured to be worn by a user, such that continuous or semi-continuous monitoring of the user's body chemistry is enabled; however, the microsensor 100 can alternatively be used intermittently to sense analytes characterizing the user's body chemistry. Preferably, the microsensor 100 is configured to penetrate the user's stratum corneum (e.g., an outer skin layer) in order to sense analytes characterizing the user's body chemistry in the user's interstitial (extracellular) fluid; however, the microsensor 100 can alternatively be configured to penetrate deeper layers of a user's skin in order to sense analytes within any appropriate bodily fluid of the user, such as the user's blood. The microsensor 100 can be configured to sense analytes/ions characterizing a user's body chemistry using a potentiometric measurement (e.g., for analytes including potassium, sodium calcium, alcohol, cortisol, hormones, etc.), using an amperometric measurement (e.g., for analytes including glucose, lactic acid, creatinine, etc.), using a conductometric measurement, or using any other suitable measurement.

As shown in FIG. 1B, the microsensor 100 can also be coupled to an electronics module 115, such that sensed analytes result in a signal (e.g., voltage, current, resistance, capacitance, impedance, gravimetric, etc.) detectable by the electronics module 115; however, analyte sensing can comprise any other appropriate mechanism using the microsensor 100. In an embodiment wherein the microsensor 100 is coupled with an electronics module 115, the microsensor 100 can also be integrated with the electronics module 115, in variations wherein the electronics module 115 is characterized by semiconductor architecture. In a first variation, the microsensor 100 is coupled to the semiconductor architecture of the electronics module 115 (e.g., the microsensor 100 is coupled to an integrated circuit comprising the electronics module 115), in a second variation, the microsensor 100 is more closely integrated into the semiconductor architecture of the electronics module 115 (e.g., there is closer integration between the microsensor 100 and an integrated circuit including the electronics module 115), and in a third variation, the microsensor 100 and the electronics module 115 are constructed in a system-on-a-chip fashion (e.g., all components are integrated into a single chip). As such, in some variations, filaments 120 the array of filaments 110 of the microsensor 100 can be directly or indirectly integrated with electronics components, such that preprocessing of a signal from the microsensor 100 can be performed using the electronics components (e.g., of the filaments 120, of the electronics module 115) prior to or after transmitting signals to the electronics module 115 (e.g., to an analog to digital converter). The electronics components can be coupled to a filament substrate, or otherwise integrated with the filaments in any suitable fashion (e.g., wired, using a contact pad, etc.). Alternatively, the electronics components can be fully integrated into the electronics module 115 and configured to communicate with the microsensor 100, or the electronics components can be split between the microsensor and the electronics module 115. The microsensor 100 can, however, comprise any other suitable architecture or configuration.

The microsensor 100 preferably senses analyte parameters using the array of filaments 110, such that absolute values of specific analyte parameters can be detected and analyzed. The microsensor 100 can additionally or alternatively be configured to sense analyte parameters using the array of filaments 110, such that changes in values characterizing specific analyte parameters or derivatives thereof (e.g., trends in values of a parameter, slopes of curves characterizing a trend in a parameter vs. another parameter, areas under curves characterizing a trend, a duration of time spent within a certain parameter range, etc.) can be detected and analyzed. In one variation, sensing by the microsensor 100 is achieved at discrete time points (e.g., every minute or every hour), and in another variation, sensing by the microsensor 100 is achieved substantially continuously. Furthermore, sensing can be achieved continuously, with signal transmission performed in a discrete or non-discrete manner (e.g., prior to or subsequent to processing of a signal). In one specific example for blood chemistry analysis, the array of filaments 110 of the microsensor 100 is configured to sense at least one of electrolytes, glucose, bicarbonate, creatinine, blood urea nitrogen (BUN), sodium, and potassium of a user's body chemistry. In another specific example, the array of filaments 110 of the microsensor 100 is configured to sense at least one of biomarkers, cell count, hormone levels, alcohol content, gases, drug concentrations/metabolism, pH and analytes within a user's body fluid.

1.1 Microsensor-Array of Filaments

The array of filaments 110 functions to interface directly with a user in a transdermal manner in order to sense at least one analyte characterizing the user's body chemistry. The array of filaments can be an array of fibers, an array of pillars, an array of microneedles, and/or any other suitable array configured to facilitate analyte detection in a user. The array of filaments 110 is preferably arranged in a uniform pattern with a specified density optimized to effectively penetrate a user's skin and provide an appropriate signal, while minimizing pain to the user. However, the array of filaments 110 can additionally or alternatively be coupled to the user in any other suitable manner (e.g., using an adhesive, using a coupling band/strap, etc.). Additionally, the array of filaments 110 can be arranged in a manner to optimize coupling to the user, such that the microsensor 100 firmly couples to the user over the lifetime usage of the microsensor 100. For example, the filaments 120 can comprise several pieces and/or be attached to a flexible base to allow the array of filaments 110 to conform to a user's body. In one variation, the array of filaments 110 is arranged in a rectangular pattern, and in another variation, the array of filaments 110 is arranged in a circular or ellipsoid pattern. However, in other variations, the array of filaments 110 can be arranged in any other suitable manner (e.g., a random arrangement). The array of filaments 110 can also be configured to facilitate coupling to a user, by comprising filaments of different lengths or geometries. Having filaments 120 of different lengths can additionally or alternatively function to allow measurement of different ions/analytes at different depths of penetration (e.g., a filament with a first length may sense one analyte at a first depth, and a filament with a second length may sense another analyte at a second depth). The array of filaments 110 can also comprise filaments 120 of different geometries (e.g., height, diameter) to facilitate sensing of analytes/ions at lower or higher concentrations. In one specific example, the array of filaments 110 is arranged at a density of 100 filaments per square centimeter and each filament 120 in the array of filaments 110 has a length of 250-350 microns, which allows appropriate levels of detection, coupling to a user, and comfort experienced by the user. In variations of the specific example, a filament 120 in the array of filaments 110 can have a length from 0-1000 m, or more specifically, a length from 150-500 μm.

Each filament 120 in the array of filaments 110 preferably functions to sense a single analyte; however, each filament 120 in the array of filaments 110 can additionally be configured to sense more than one analyte. Furthermore, the array of filaments 110 can be further configured, such that a subarray of the array of filaments 110 functions as a single sensor configured to sense a particular analyte or biomarker. As shown in FIG. 1B, multiple subarrays of the array of filaments 110 may then be configured to sense different analytes/biomarkers, or the same analyte/biomarker. Furthermore, a subarray or a single filament 120 of the array of filaments 110 can be configured as a ground region of the microsensor 100, such that signals generated by the microsensor 100 in response to analyte detection can be normalized by the signals generated by the subarray or single filament 120 serving as a ground region. Preferably, all subarrays of the array of filaments 110 are substantially equal in size and density; however, each subarray of the array of filaments 110 can alternatively be optimized to maximize signal generation and detection in response to a specific analyte. In an example, analytes that are known to have a lower concentration within a user's body fluid (e.g., interstitial fluid, blood) can correspond to a larger subarray of the array of filaments 110. In another example, analytes that are known to have a lower concentration within a user's body fluid can correspond to a smaller subarray of the array of filaments 110. In one extreme example, an entire array of filaments can be configured to sense a single analyte, such that the microsensor 100 is configured to sense and detect only one analyte.

In other variations, a subarray of the array of filaments 117 (FIG. 5C) can also be used to detect other physiologically relevant parameters, including one or more of: electrophysiological signals (e.g., electrocardiogram, electroencephalogram), body temperature, respiration, heart rate, heart rate variability, galvanic skin response, skin impedance change (e.g., to measure hydration state or inflammatory response), and any other suitable biometric parameter. In these other variations, the subarray would be dedicated to measuring these physiologically relevant parameters, which could be combined with analyte/ion parameter measurements in order to provide meaningful information to a user. As an example, the simultaneous measurement of potassium levels and electrocardiogram measurements, enabled by subarrays of the array of filaments 117 (FIG. 5C), may provide a more complete diagnosis of cardiovascular problems or events than either measurement by itself.

1.2 Microsensor-Filament

As shown in FIG. 2A, each filament 120 of the array of filaments 110 comprises a substrate 130 and a conductive layer 140 configured to facilitate analyte detection. Each filament 120 of the array of filaments 110 can further comprise an insulating layer 150 configured to isolate regions for analyte detection, a sensing layer 160 configured to enable transduction of an ionic concentration to an electronic voltage, and a selective coating 170 configured to facilitate detection of specific target analytes. As shown in FIG. 2E, each filament can further comprise an adhesion coating 180 configured to maintain contact between layers, coatings, and/or substrates of the filament 120, and/or a temporary functional layer 190, as shown in FIG. 2F, configured to facilitate penetration of a filament 120 into the body. A filament 120 thus functions to directly penetrate a user's skin, and to sense specific target analytes/ions characterizing the user's body chemistry.

The substrate 130 functions to provide a core or base structure upon which other layers or coatings can be applied, in order to facilitate processing of each filament 120 for specific functionalities. As such, the material of which the substrate 130 is composed can be processed to form at least one protrusion as a substrate core for a filament 120, including a base end coupled to the substrate 130 bulk and a tip at the distal end of the substrate core, that facilitates access to a body fluid of the user. Alternatively, the substrate 130 can be coupled to a protrusion (e.g., as a piece separate from the substrate) or a protrusion can be grown from a surface of the substrate 130 in any other suitable manner. Preferably, the material of the substrate 130 is processable to form an array of protrusions as substrate cores for the array of filaments 110; however, the material of the substrate 130 can alternatively be processable in any other suitable manner to form any other suitable filament structure. Preferably, the substrate 130 has a uniform composition; however, the substrate 130 can alternatively have a non-uniform composition comprising regions or layers configured to facilitate processing of subsequent functional layer/coating additions. The substrate 130 can be composed of a semiconducting material (e.g., silicon, quartz, gallium arsenide), a conducting material (e.g., gold, steel, platinum, nickel, silver, polymer, etc.), and/or an insulating or non-conductive material (e.g., glass, ceramic, polymer, etc.). In some variations, the substrate 130 can comprise a combination of materials (e.g., as in a composite, as in an alloy). Furthermore, in variations wherein the substrate 130 is non-conductive, a fluid path defined at the substrate 130 (e.g., a fluid channel, a groove, a hollow region, an outer region, etc.) and coupled to a conductive layer 140 (e.g., a conductive base region, a conductive core, a conductive outer layer) can enable signal transmission upon detection of an analyte/analyte concentration. In a specific example, the substrate 130 is composed of P-type, boron-doped, <100> orientation silicon with a resistivity of 0.005-0.01 ohm-cm, a thickness from 500-1500 μm, a total thickness variation (TTV) of <10 μm, with a first surface side polish. In variations of the specific example, the substrate 130 can be composed of silicon with any other suitable type, doping, miller index orientation, resistivity, thickness, TTV, and/or polish. Furthermore, the substrate 130 can be processed using semiconductor processing methods, machining methods, manufacturing processes suited to a ductile substrate material, and/or manufacturing methods suited to a brittle material.

The conductive layer 140 functions to provide a conductive "active" region to facilitate signal transmission upon detection of an analyte by a filament 120. The conductive layer 140 can comprise a layer of a single material, or can alternatively comprise multiple materials (e.g., multiple layers of one or more materials). In variations, the conductive layer 140 can include any one or more of: a platinum-based material, an iridium-based material, a tungsten-based material, a titanium-based material, a gold-based material, a nickel-based material, and any other suitable conductive or semiconducting material (e.g., silicon, doped silicon). Furthermore, the layer(s) of the conductive layer 140 can be defined by any suitable thickness that allows signal transmission upon detection of an analyte by the filament 120. In a first specific example, the conductive layer 140 includes a 1000 Å thick platinum layer, a 1000 Å thick iridium layer, a 1000 Å thick tungsten layer, and a 100 Å thick titanium nitride layer. In a second specific example, the conductive layer 140 includes a 1000 Å thick platinum layer and a 100 Å thick titanium layer. In a third specific example, the conductive layer 140 includes a 1000 Å thick platinum layer and a 100 Å thick titanium nitride layer. In a fourth specific example, the conductive layer 140 includes a 1000 Å thick iridium layer and a 100 Å thick titanium nitride layer. In a fifth specific example, the conductive layer 140 includes a 1000 Å thick tungsten layer. In a sixth specific example, the conductive layer 140 includes one or more of: nickel, gold, and platinum (e.g., deposited by electroplating). Preferably, the conductive layer 140 only covers a portion of the substrate 130 (e.g., a substrate core) contacting the user's body fluids, thus forming an "active region" of the filament 120, and in one variation, covers a tip region of each filament 120 (e.g., a tip of a substrate core); however, the conductive layer 140 can alternatively cover the entire surface of the substrate 130 contacting a user's body fluids. In variations wherein the substrate 130 is conductive, the filament 120 can altogether omit the conductive layer 140. Furthermore, in variations wherein the substrate 130 is non-conductive, a fluid path defined at the substrate 130 (e.g., a fluid channel, a groove, a hollow region, an outer region, etc.) and coupled to a conductive layer 140 (e.g., a conductive base region, a conductive core, a conductive outer layer) can enable signal transmission upon detection of an analyte/analyte concentration, as described above.

The insulating layer 150 functions to form an insulating region of a filament 120, and is configured to provide a "non-active" region of the filament 120. Additionally, the insulating layer 150 functions to define and/or isolate an "active" region of the filament 120. As such, the insulating layer 150 preferably leaves at least a portion of the conductive layer 140 exposed to define the active region of the filament 120. In one variation, the insulating layer 150 ensheathes the substrate core of each filament 120 in the array of filaments, and can additionally or alternatively cover all exposed regions of the substrate 130 to isolate areas of signal transmission. The insulating layer 150 preferably includes an oxide layer that is grown at desired surfaces of the substrate (e.g., to a thickness of 0.1-10 μm), thereby forming the insulating layer. However, the insulating layer 150 can additionally or alternatively include any other suitable material that is not removable during removal of sacrificial layers used during processing of the array of filaments 110. As such, in other variations, the insulating layer 150 can be composed of any one or more of: an insulating polymer (e.g., polyimide, cyanate ester, polyurethane, silicone) that is chemical and/or heat resistant, an oxide, a carbide, a nitride (e.g., of silicon, of titanium), and any other suitable insulating material. Preferably, the insulating layer 150 only covers a portion of the substrate contacting the user's body fluids, thus defining an "active region" of the filament 120 and a "non-active" region of the filament 120. Alternatively, the filament 120 can altogether omit the insulating layer 150.

The sensing layer 160 functions to enable transduction of an ionic concentration to an electronic voltage, to enable measurement of analyte/ion concentrations characterizing body chemistry. The sensing layer 160 can also function to prevent unwanted signal artifacts due to oxygen fluxes in a user's body fluids. Furthermore, the sensing layer 160 can also enable transduction of a molecular species concentration through a current, capacitance, or resistance change. Preferably, the sensing layer is a conductive material with reversible redox reaction behavior, such that detection of increased ion concentrations followed by decreased ion concentrations (or visa versa) can be enabled by the sensing layer 160. Additionally, the sensing layer 160 is preferably an appropriately bio-safe, anti-inflammatory, and anti-microbial material. The sensing layer 160 can be a polymer, such as polypyrrole or polyaniline, which undergoes a reversible redox reaction characterized by the following generic equation: $P^{(ox)}+e-\Leftrightarrow P^{(red)}$. The sensing layer 160 can additionally or alternatively be composed of any appropriate conductive material (e.g., sulfur-containing polythiophenes, silver chloride, etc.) that has reversible redox reaction behavior. For example, silver chloride undergoes a reversible redox reaction characterized by the following equation: $AgCl+e-\Leftrightarrow Ag(s)^{+}+Cl^{-}$. In either example redox reaction equation, electron (e−) generation results in measurable signals corresponding to detected ion concentrations for analyte detection, and further, the sensing layer 160 serves as a reference electrode for ion concentration measurements based upon a detected voltage change across a selective coating 170 coupled to the sensing layer 160. However, in other variations, the sensing layer 160 may not comprise a material with reversible redox reaction behavior, and other variations can further comprise a controlled ion coating (e.g., poly-hydroxyl ethyl methacrylate prepared with potassium chloride) that functions to form a portion of a reference electrode for ion concentration measurements.

Additionally or alternatively, the sensing layer 160 can include molecules that facilitate analyte detection. In variations, the sensing layer can include one or more amine-decorated polymer materials. For instance, in examples, the amine-decorated polymer material(s) implemented can include one or more of: tyramine, phenylenediamine, lysine, and any other suitable amine-decorated polymer.

In one example, the sensing layer 160 includes electropolymerized phenylenediamine, tyramine, glucose oxidase, and poly-lysine to facilitate glucose sensing. The sensing layer 160 is preferably uniform over an active region of a filament 120 defined by the conductive layer 140 and the insulating layer 150; however, the sensing layer 160 can alternatively non-discriminately coat the surface of the filament 120, and/or can be a non-uniform coating. The sensing layer 160 can be maintained at a viable state by packaging the microsensor 100 in a hydrated state; however, the sensing layer 160 can be alternatively be configured to equilibrate within a short time period (e.g., less than one hour) upon coupling of the array of filaments 110 to a user. Alternative variations of the filament may altogether omit the sensing layer 160.

The selective coating 170 functions to facilitate sensing of specific target analytes. The selective coating 170 preferably facilitates ion-selective reactions that generate signals reflective of ion concentration; however, the selective coating 170 can additionally or alternatively facilitate enzyme reactions that generate changes in signals (e.g., current) due to binding of complementary molecules to target analytes/ions. The selective coating 170 is preferably anti-microbial and anti-inflammatory, and can additionally or alternatively include any other features that encourage biocompatibility during use by a user. Preferably, the selective coating 170 comprises at least one complementary molecule 171 (e.g., ionophore, protein, peptide, amino acid, etc.) to a target analyte/ion distributed within a polymer matrix 172, as shown in FIG. 2A. Preferably, the complementary molecule 171 is evenly dispersed throughout the polymer matrix 172; however, the complementary molecule 171 can alternatively be localized within regions of the polymer matrix 172 in a heterogeneous manner. In examples, the complementary molecule is valinomycin/potassium tetrakis for potassium sensing, 4-tert-Butylcalix [4] arene-tetraacetic acid tetraethyl ester for sodium sensing, (−)-(R,R)-N,N'-Bis-[11-(ethoxycarbonyl) undecyl]-N,N',4,5-tetramethyl-3,6-dioxaoctane-diamide, Diethyl N,N'-[(4R,5R)-4,5-dimethyl-1,8-dioxo-3,6-dioxaoctamethylene]bis(12-methylaminododecanoate) for calcium sensing, and meso-Tetraphenylporphyrin manganese (III)-chloride complex for chloride sensing, according to ion-selective reactions. In an example, the polymer matrix 172 is composed of polyvinyl chloride (PVC) with a plasticizer to affect flexibility of the polymer matrix; however, the polymer matrix 172 can additionally or alternatively be composed of any other suitable polymer (e.g., polyethylene, polytetrafluoroethylene, urethane, parylene, nafion, polyvinyl chloride, polyvinyl alcohol (e.g., without additional crosslinking agents), chitosan, polyvinyl butyral, polydimethylsiloxane, fluorinated polymers, cellulose acetate, etc.) or non-polymer (e.g., oxide, nitride, carbide, etc.) configured to contain a distribution of complementary molecules. Additionally, the selective coating 170 may not comprise a plasticizer. The selective coating 170 is preferably defined by a thickness that characterizes a rate at which complementary molecules bind to target analytes (e.g., diffusion rate), and that also characterizes the amount (e.g., concentration or total amount) of complementary molecules within the selective coating 170. Additionally, the polymer matrix 172 can contain additives and can additionally or alternatively be processed (e.g., with polar functional groups) to improve its adhesion to the filament 120 and to prevent delamination as the filament 120 is inserted into a user's skin. In examples, additives of the polymer matrix 172 can include amino-silanes, polyhydroxy-ether imides, butylated silica, and heterogeneous oxidizers.

In other variations, the selective coating 170 of the filament 120 can additionally or alternatively function to enable amperometric detection of molecules (e.g., glucose, creatinine) using immobilized enzymes. In these variations, the selective coating 170 can be replaced by or may further comprise a layer of immobilized enzyme (e.g., glucose oxidase for glucose, creatine amidinohydrolase for creatinine) that functions to catalyze a reaction of the analyte to produce a mediator species (e.g., hydrogen peroxide), wherein the concentration of the mediator species can be amperometrically detected via oxidation or reduction at a surface of the conductive layer 140 or the sensing layer 160. In one example, glucose is oxidized by glucose oxidase to generate hydrogen peroxide. The generated hydrogen peroxide is then hydrolyzed by a conducting surface (e.g., a platinum conducting layer) while it is held at an electric potential. In a variation of this example, the conducting surface may alternatively not be held at an electric potential, for instance, in cases wherein molecular or other species (e.g., iron hexacyanoferrate) serve as a layer of transduction. Furthermore, in other variations of this example, other oxidases (e.g. alcohol oxidase, D- and L-amino acid oxidases, cholesterol oxidase, galactose oxidase, urate oxidase, etc.) can be used in a similar manner for the analysis of their complements.

In variations of the sensing layer including a layer of immobilized enzymes, the layer of immobilized enzymes can be covered by one or more membranes, which functions to control the diffusion rate and/or concentrations of analyte, mediator species (e.g., hydrogen peroxide, ferrocene), or interfering species (e.g., uric acid, lactic acid, ascorbic acid, acetaminophen, oxygen). The membrane(s) can also function to provide mechanical stability. In examples, the membrane(s) can include any one or more of: polyurethanes, nafion, cellulose acetate, polyvinyl alcohol (e.g., without additional crosslinking agents), chitosan, polyvinyl chloride, polydimethylsiloxane, parylene, polyvinyl butyrate and any other suitable membrane material.

As shown in FIG. 2E, any filament 120 of the array of filaments 110 can further comprise an adhesion coating 180, which functions to maintain contact between layers, coatings, and/or substrates of the filament 120. The adhesion coating 180 can further function to bond the layers, coatings, and/or substrates, and can prevent delamination between the layers, coatings, and/or substrates. The adhesion coating 180 is preferably an appropriately bio-safe, anti-inflammatory, and anti-microbial material, and preferably maintains contact between layers, coatings, and/or substrates of the filament 120 over the lifetime usage of the microsensor 100. In examples, the adhesion coating 180 is composed of any one or more of: a polyurethane, nafion, cellulose acetate, polyvinyl alcohol (e.g., without additional crosslinking agents), chitosan, polyvinyl butyrate, polyvinyl chloride, polydimethylsiloxane, paralyene, any material used in variations of the selective coating 170, and any other suitable adhesion material. However, in variations, a filament 120 of the microsensor 100 can alternatively not comprise an adhesion coating 180. Alternatively, layers, coatings, and/or substrates of the filament can be treated (e.g., heat treated, ultraviolet radiation treated, chemically bonded, etc.) and/or processed such that appropriate contact is maintained, even without an adhesion coating 180.

As shown in FIG. 2F, any filament 120 can further comprise a temporary functional layer 190, which functions to facilitate penetration of a filament 120 into the body. After the filament 120 has penetrated the body, the temporary functional layer 190 is preferably configured to dissolve or be absorbed by the body, leaving other portions of the filament 120 to operate to detect target analytes/ions characterizing a user's body chemistry. The temporary functional layer 190 can be configured, such that the sensing layer 160 is at an appropriate depth for detection (e.g., has access to interstitial fluid below the user's stratum corneum), once the temporary functional layer 190 has penetrated the user's body. The temporary functional layer 190 is preferably composed of an inert, bioabsorbable material that is porous; however, the temporary functional layer 190 can alternatively not be porous or bioabsorbable. In some variations, the temporary functional layer 190 can be configured to release an initial ion concentration with a known release profile (e.g., spiked or continuous release) in order to calibrate the microsensor 100. In specific examples, the temporary functional layer 190 can include a nitride material (e.g., 1000-2500 Å thick nitride), an oxide material, a carbide material, a salt, a sugar, a polymer (e.g., polyethylene glycol), and/or any other suitable material that does not deteriorate during subsequent processing steps. Other variations of the filament can further comprise any other suitable temporary functional layer 190 providing any other suitable function.

Any filament 120 of the microsensor 100 can further comprise any other appropriate functional layer or coating. In variations, a filament 120 can comprise layers or coatings that perform any one or more of the following functions: suppress or prevent an inflammatory response (e.g., by comprising a surface treatment or an anti-inflammatory agent), prevent bio-rejection, prevent encapsulation (e.g., by comprising a bio-inert substance, such as pyrolytic carbon), enhance target analyte/ion detection, and provide any other suitable anti-failure mechanism for the array of filaments 110. In one such variation, a filament 120 of the microsensor 100 can include a biocompatible layer 185 appropriately situated (e.g., situated deeper than a temporary functional layer 190, situated superficial to an adhesion layer, etc.) to enhance biocompatibility of the filament 120. In examples, the biocompatible layer 185 can include a polymer (e.g., urethane, parylene, teflon, fluorinated polymer, etc.) or any other suitable biocompatible material. In another variation, a filament 120 of the microsensor 100 can additionally or alternatively include an intermediate protective layer 166 appropriately situated (e.g., situated deeper than a selective layer 170, etc.), which functions as an optional layer to provide intermediate protection and/or block transport of undesired species. In examples, the intermediate protective layer can include a polymer (e.g., teflon, chlorinated polymer, nafion, polyethylene glycol, etc.) and can include functional compounds (e.g., lipids, charged chemical species that block transport of charged species, etc.) configured to provide a protective barrier. In another variation, a filament 120 of the microsensor 100 can additionally or alternatively include a stabilizing layer 163 appropriately situated (e.g., situated deeper than an intermediate protective layer 166, situated deeper than a selective layer 170, situated superficial to a sensing layer 160, etc.), which functions to stabilize the sensing layer 160. In one example, the stabilizing layer 163 can include a polymer (e.g., an amine-deccorated polymer, such as electropolymerized phenylenediamine) acting to stabilize a glucose-oxidase sensing layer 160. In another variation, a filament 120 of the microsensor 100 can additionally or alternatively include an intermediate selective layer 145 appropriately situated (e.g., situated deeper than a sensing layer 160, situated superficial to a conductive layer 140, etc.), which functions to provide an additional selective layer. The intermediate selective layer can include or be coupled to an immobilized complementary molecule (e.g., glucose oxidase) to facilitate analyte detection. In an example, the intermediate selective layer 145 includes a polymer (e.g., an amine-decorated polymer, such as electropolymerized phenylenediamine) and is situated superficial to a conductive layer 140; however, in variations of the example, the intermediate selective layer 145 can include any other suitable selective material and can be situated relative to other layers in any other suitable manner. In another variation, a filament 120 of the microsensor 100 can additionally or alternatively include an intermediate active layer 143 appropriately situated (e.g., situated deeper than an intermediate selective layer 145, situated deeper than a sensing layer 143, situated superficial to a conductive layer 140, etc.), which functions to facilitate transduction of a signal. As such, the intermediate active layer 143 can facilitate transduction in variations wherein the conductive layer 140 is not held at a given potential, and/or can facilitate transduction in any other suitable manner. In one example, the intermediate active layer 143 comprises iron hexacyanoferrate (i.e., Prussian Blue) and in another example, the intermediate active layer 143 comprises nano-Platinum; however, the intermediate active layer 143 can additionally or alternatively include any other suitable material.

In any of the above embodiments, variations, and examples, any one or more of layers 185, 166, 163, 145, 143 can be isolated to a desired region of the filament 120, or can non-discriminately coat an entire surface of the filament 120 at a given depth. Furthermore, any filament 120 of the microsensor 100 can include multiple instances of any layer or coating 140, 143, 145, 150, 160, 163, 166, 170, 180, 185 190, can omit a layer or coating 140, 143, 145, 150, 160, 163, 166, 170, 180, 185 190, and/or can include layers or coatings arranged in any other suitable manner different from the variations and examples described above and below. In one such variation, a different configuration of layers can allow selective passage of molecules having different properties (e.g., chemistries, size). However, any suitable configuration of a filament 120 can be provided for any other suitable application.

As shown in FIG. 3, each filament 120 of the array of filaments 110 can have one of a variation of geometries. In a first geometric variation a filament 120 can be solid, examples of which are shown in FIGS. 3B and 3D-3G. In a first example of the solid filament 120a, the solid filament 120a can have a profile tapering continuously to at least one point (e.g., pyramid or conical shaped with one or more pointed tips), and can have straight or curved edges, as shown in FIGS. 3B, 3D, and 3G. In variations, the point(s)

of the filament 120 can be defined by any suitable number of faces. In a second example of the solid filament 120a, the solid filament 120a can comprise two regions—a pointed tip region 121 configured to pierce a user's skin, and a blunt region 122 (e.g., a columnar protrusion, a pillar), coupled to the pointed tip region, as shown in FIG. 3E. The pointed tip region 121 can be configured to be bioabsorbable, dissolve (e.g., using a degradable material) or, in an extreme example, break off (e.g., using an engineered stress concentration) and be expelled from a user's system after the solid filament 120a has penetrated the user's skin; however, the pointed tip region 121 can alternatively be configured to remain attached to the solid filament 120a after the solid filament 120a has penetrated the user's skin. In a third example of the solid filament 120a, the solid filament 120a can comprise two regions—a barbed tip region 123 including a barb configured to penetrate a user's skin and promote skin adherence, and a second region 122 coupled to the barbed tip region, as shown in FIG. 3F. In the third example of the solid filament 120a, the barbed tip region can be configured to have one sharp protrusion for skin penetration, or can alternatively be configured to have multiple sharp protrusions for skin penetration.

In a second geometric variation, examples of which are shown in FIGS. 3A, 3C, and 3H, a filament 120 can be hollow and comprise a channel 125 within an interior region of the hollow filament 120b. In a first example of the hollow filament 120b, the hollow filament 120b can have a profile tapering continuously to at least one point (e.g., pyramid or conical shaped with one or more pointed tips), and can have straight or curved edges. Furthermore, the point(s) of the filament 120 can be defined by any suitable number of faces. In the first example of the hollow filament 120b, the hollow filament 120b can additionally be processed to have one or more channels 125 configured to facilitate sensing of an analyte characterize a user's body chemistry. In the first example, a channel 125 of the hollow filament 120b can be characterized by a uniform cross section along the length of the channel 125, or can alternatively be characterized by a non-uniform cross section along the length of the channel 125. In a second example of a hollow filament 120b, the hollow filament 120b can be configured to receive a volume of the user's body fluid into a sensing chamber to facilitate analyte detection. In the second geometric variation, the hollow filament 120b can be composed of a metal or a semiconductor, or any appropriate material to facilitate analyte sensing. In other examples, the hollow filament 120b may implement a variation of any of the solid filaments described above, but be processed to have at least one channel 125 within an interior region of the hollow filament 120b. Each filament 120 in the array of filaments 110 can include a combination of any of the above geometric variations, a different variation of the above geometric variations, and furthermore, the array of filaments 110 can comprise filaments characterized by different geometric variations.

In a first specific example of a filament 120, as shown in FIG. 2A, a solid filament 120a comprises a uniform silicon substrate 130 composed to P-type, boron-doped orientation <100> silicon with a resistivity from 0.005-0.01 ohm-cm, a thickness of 500-1500 μm, and a TTV less than 10 μm, processed to define a substrate core with a pointed tip region 121 formed by way of a dicing saw, as described in Section 2 below. In the first specific example, the filament comprises a conductive layer 140 of nickel, coupled to the substrate 130 by electroplating, wherein the conductive layer 140 is isolated to the pointed tip region 121 of the substrate core, and to a face of the substrate 130 directly opposing the face including the filament 120. In the first specific example, the filament 120 further includes an insulating layer 150 of 1 μm oxide, formed by thermal growth at 900-1050 C for 1-2 hours, as described in further detail below, wherein the insulating layer 150 is formed at all exposed surfaces of the substrate 130 and defines an active region at the pointed tip region 121 of the filament 120. In variations of the first specific example, the conductive layer 140 can additionally or alternatively include one or more of a gold-based material and a platinum-based material. Furthermore, in the first specific example, the filament 120 can include a conductive polymer (polypyrrole) coating as the sensing layer 160 coupled to the conductive layer 140 at the pointed tip region 121 of the filament 120, and a PVC selective coating 170 with complementary molecules 171 to target analytes coupled to the sensing layer 160. In the first specific example, the solid filament 120a includes a rectangular prismatic columnar protrusion, with a pointed tip region defined by four faces tapering to a point, as shown in FIG. 5C, wherein two of the four faces are orthogonal to each other and contiguous with two faces of the rectangular prismatic columnar protrusion, and wherein the other two faces are formed by way of a dicing saw with an angled blade, as described further in Section 2 below.

In a second specific example of a filament 120 for glucose sensing, which can be characterized as shown in FIG. 2B, a solid filament 120a comprises a uniform silicon substrate 130 composed to P-type, boron-doped orientation <100> silicon with a resistivity from 0.005-0.01 ohm-cm, a thickness of 500-1500 μm, and a TTV less than 10 μm, processed to define a substrate core with a pointed tip region 121 formed by way of a dicing saw, as described in Section 2 below. In the second specific example, the filament comprises a conductive layer 140 of nickel, gold, and platinum, coupled to the substrate 130 by electroplating, wherein the conductive layer 140 is isolated to the pointed tip region 121 of the substrate core, and to a face of the substrate 130 directly opposing the face including the filament 120. In the second specific example, the filament 120 further includes an insulating layer 150 of 0.1-10 μm oxide, formed by thermal growth at 900-1050 C for 1-2 hours, as described in further detail below, wherein the insulating layer 150 is formed at all exposed surfaces of the substrate 130 and defines an active region including the conductive layer 140 at the pointed tip region 121 of the filament 120. Furthermore, in the second specific example, the filament includes electropolymerized phenylenediamine, tyramine, glucose oxidase, and poly-lysine as the sensing layer 160 superficial to the conductive layer 140 at the pointed tip region 121 of the filament 120. In between the conductive layer 140 and the sensing layer 160 at the pointed tip region 121, the second specific example includes an intermediate selective layer 145 of electro-polymerized phenylenediamine polymer coupled to an intermediate active layer 143 including iron hexacyanoferrate, coupled directly to the conductive layer 140. Finally the second specific example includes an intermediate protective layer 166 of urethane, coupled to a stabilizing layer 163 of phenylenediamine (or other polymer, or other amine-decorated polymer) coupled to the sensing layer 160, surrounded by a PVC selective coating 170 with complementary molecules 171 to target analytes coupled to the sensing layer 160. In the second specific example, the solid filament 120 is includes a rectangular prismatic columnar protrusion, with a pointed tip region defined by four faces tapering to a point, as shown in FIG. 5C, wherein two of the four faces are orthogonal to each other and contiguous with two faces of the rectangular prismatic columnar protrusion, and wherein the other two faces are formed by way of a dicing saw with an angled blade, as described further in Section 2 below.

Figure 2C:
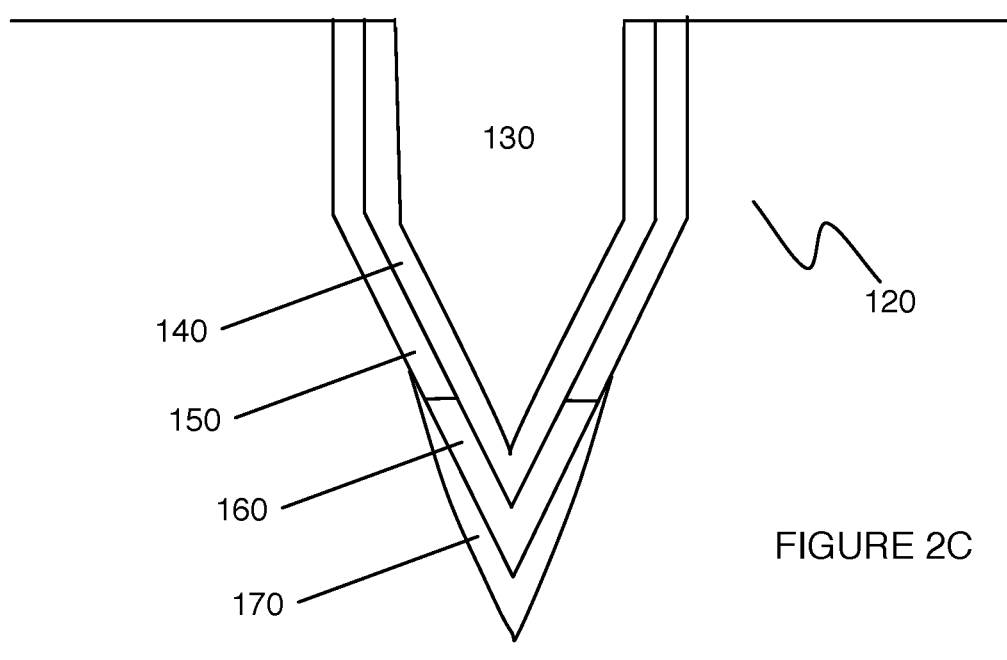
FIGS. 2C and 2D depict examples of filaments for biomonitoring.

In a third specific example of a filament 120, as shown in FIG. 2C, a solid filament 120a comprises a uniform silicon substrate 130, a conductive layer 140 of platinum at the tip of the filament 120, an insulating layer 150 composed of polyimide isolating the active region of the filament 120 to the tip of the filament, a conductive polymer (polypyrrole) coating as the sensing layer 160, and a PVC selective coating 170 with complementary molecules 171 to target analytes. In the third specific example, the solid filament 120 is conical and has a profile tapering to a single sharp point.

Figure 2D:
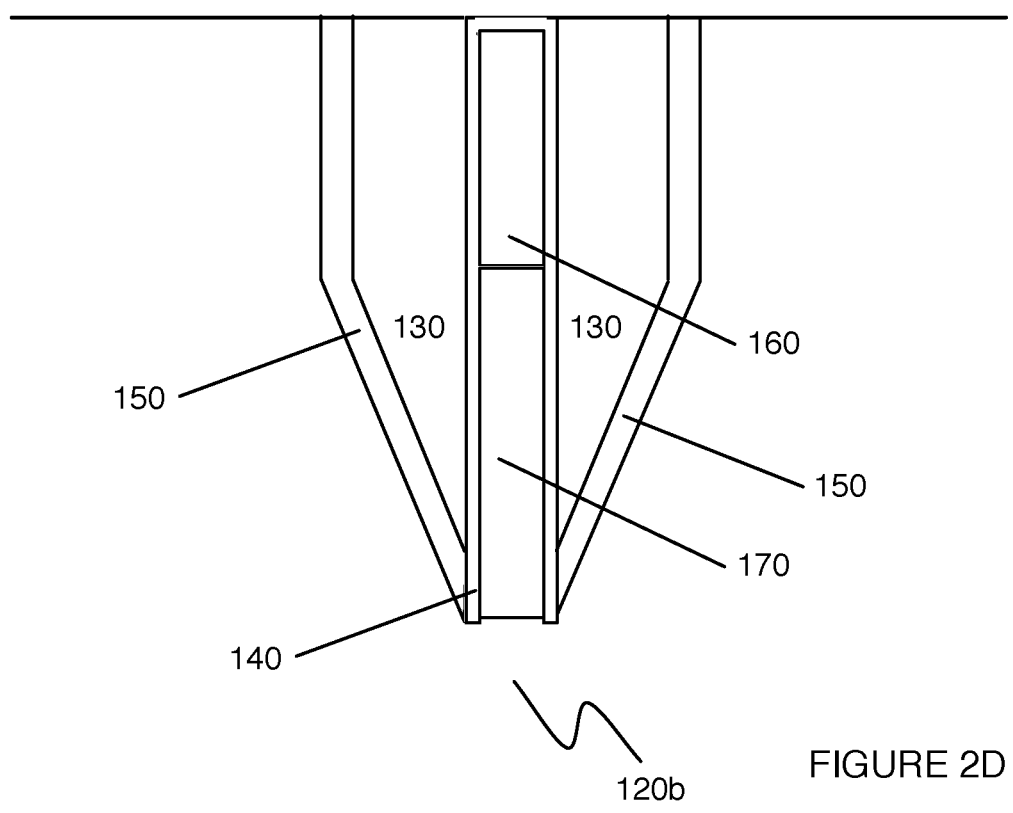
Figure 2E:
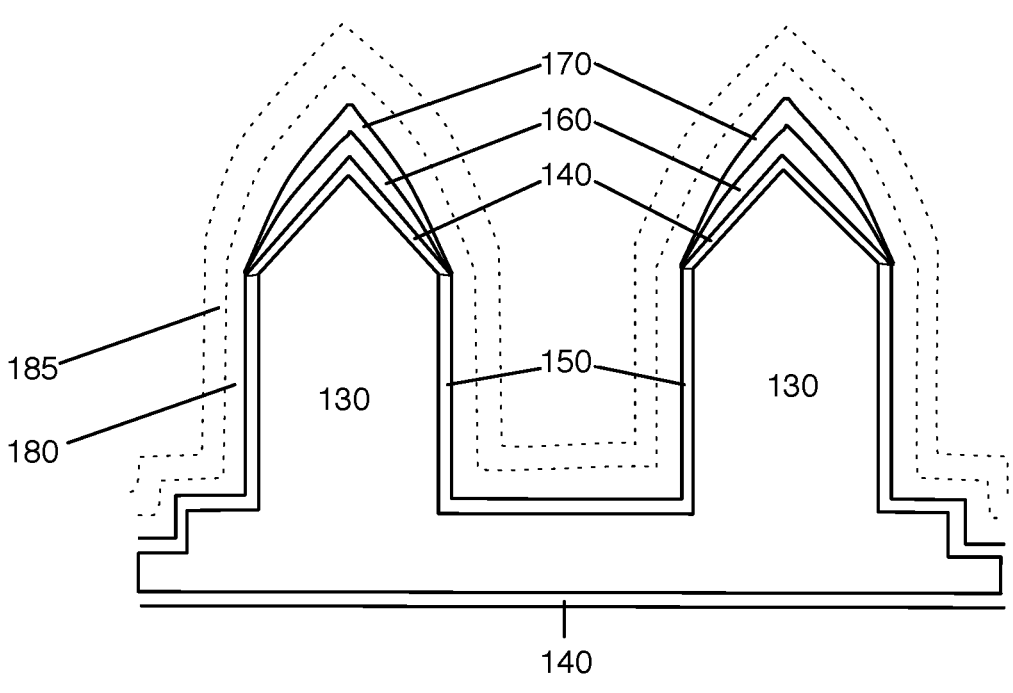
FIG. 2E depicts an example of a filament, comprising an adhesion layer, for biomonitoring.
Figure 2F:
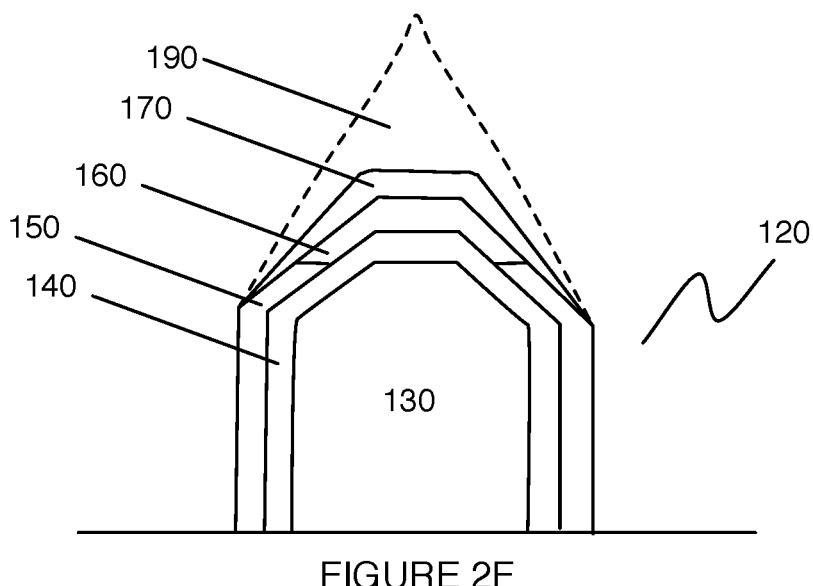
FIG. 2F depicts an example of a filament, comprising a temporary functional layer, for biomonitoring.

In a fourth specific example of a filament 120, as shown in FIG. 2D, a hollow filament 120b comprises a uniform silicon substrate 130, an external surface coated with an insulating layer 150 composed of polyimide, a conductive layer 140 of platinum covering the surface of an interior channel 125, a conductive polymer (polypyrrole) coating as a sensing layer 160 covering the conductive layer 140 of platinum, and a selective PVC coating 170 covering the sensing layer 160. In the fourth specific example, the hollow filament 120b is conical with a single cylindrical channel 125 passing through the axis of rotation of the conical filament 120.

Each filament 120 in the array of filaments 110 can also be structured as any appropriate combination of the above variations and/or examples of filament 120 composition and/or geometry, and/or can be paired with a filament 120 serving as a reference electrode configured to normalize a signal detected in response to analyte sensing. Additionally, the array of filaments 110 can comprise filaments characterized by different variations of filament composition (e.g., composition of layers and/or coatings).

2. Manufacturing Method

As shown in FIG. 4, an embodiment of a manufacturing method 200 for the microsensor comprises forming a filament substrate S210; applying a conductive layer to the filament substrate S220; defining an active region and a non-active region of the filament with an insulating layer S230; applying a sensing layer to at least the conductive layer S240; and forming a selective layer S250, coupled to the sensing layer, configured to target at least one specific analyte characterizing body chemistry. The manufacturing method 200 functions to form an array of filaments as part of a microsensor for monitoring body chemistry. Preferably, the manufacturing method 200 forms an array of substantially identical filaments, wherein each filament in the array of filaments comprises an active region for analyte detection, and a non-active region comprising an insulating layer. Alternatively, the manufacturing method 200 can form an array of substantially non-identical filaments, with different portions of the array having different functionalities and/or configurations.

Figure 5A:
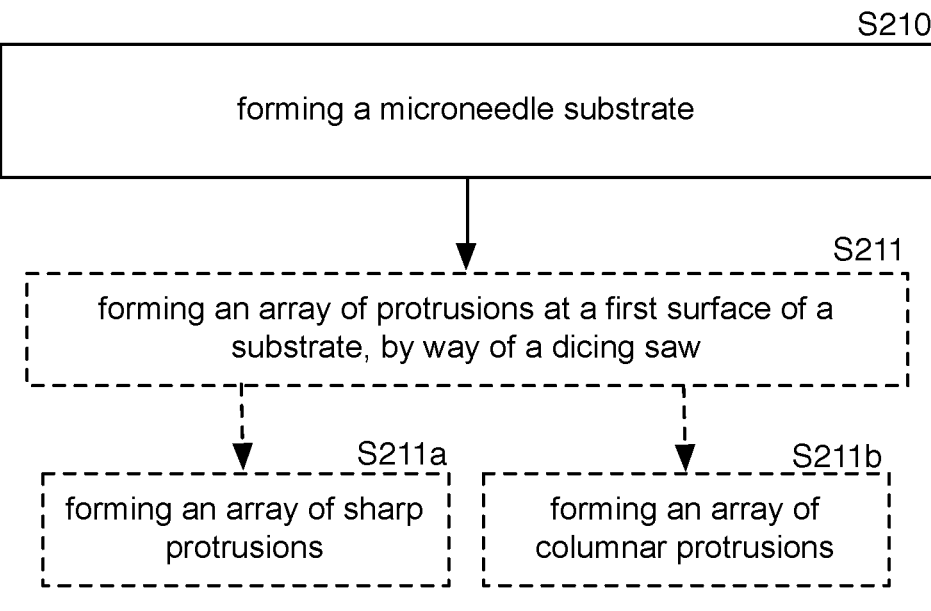
Figure 5B:
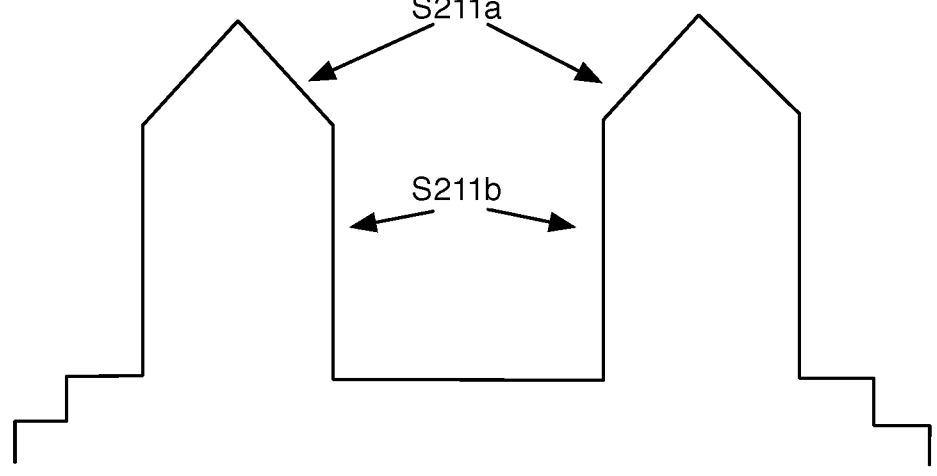

2.1 Manufacturing Method-Substrate, Conductive Layer, and Insulating Layer Processing Block S210 recites forming a filament substrate, and functions to form a core or base structure upon which other layers or coatings can be applied, in order to facilitate processing of each filament for specific functionalities. As shown in FIG. 5A, in a first variation, Block S210 includes forming an array of protrusions at a first surface of the substrate, by way of a dicing saw S211. In variations of Block S211, forming an array of protrusions can include forming an array of sharp protrusions S211a, as shown in FIGS. 5B and 5C, by way of an angled blade (e.g., a 60 degree blade, a 45 degree blade) of a dicing saw or other saw characterized by a desired depth (e.g., 150-500 µm), configured to cut a desired number of facet-filament tips (e.g., 2-facet tips, 4-facet tips, 6-facet tips, etc.) at a desired rate (e.g., 1-10 mm/s). In block S211a, the dicing saw can be configured to form the array of sharp protrusions through adjacent cuts in a first direction, followed by adjacent cuts in a second direction (e.g., orthogonal to the first direction), thereby forming a 2-dimensional array of sharp protrusions (i.e., sharp tips). However, any suitable number of cuts in any suitable number of directions can be used to form the array. Additionally or alternatively, forming the array of protrusions in Block S211 can including forming an array of columnar protrusions S211b at the first surface of the substrate, by way of a non-angled blade of a dicing saw of a desired depth (e.g., 25-500 µm) and width (e.g., 75-200 µm) with a desired gap (e.g., 25-2000 µm), configured to cut a desired number of columnar protrusions at a desired rate (e.g., 1-10 mm/s), wherein each columnar protrusion defines any suitable cross sectional profile (e.g., polygonal, non-polygonal). In block S211b, the dicing saw can be configured to form the array of columnar protrusions through adjacent cuts in a first direction, followed by adjacent cuts in a second direction (e.g., orthogonal to the first direction), thereby forming a 2-dimensional array of columnar protrusions. However, any suitable number of cuts in any suitable number of directions can be used to form the array.

In variations of Block S211, Blocks S211a and S211b preferably form protrusions with a sharp tip defined at the end of each columnar protrusion in a one-to-one manner, as shown in FIG. 5B, wherein the sharp tip is substantially aligned with and contiguous with a respective columnar protrusion; however, the sharp tip(s) can be non-aligned with a respective columnar protrusion, can be non-contiguous with a respective columnar protrusion, and/or can be formed in a non-one-to-one manner with the array of columnar protrusions. In some variations, a sharp tip can comprise a pyramidal tip region defined by an irregular pyramid, having a first pair of orthogonal faces, substantially contiguous with two faces of the columnar protrusion, and a second pair of orthogonal faces, angled relative to the first pair of orthogonal faces, such that the tip is substantially aligned with a vertex of the rectangular cross section of the columnar protrusion; however, in other variations, the tip can be misaligned with a vertex of the rectangular cross section of the columnar protrusion. Furthermore, Blocks S211a and S211b can be performed in any suitable order, in order to facilitate application of the conductive layer to the filament substrate in variations of Block S220 and/or defining an active region and a non-active region of the filament with an insulating layer, in variations of Block S230. In still further variations, alternatives to the first variation of Block S210 can include forming the array of protrusions at the first surface of the substrate by way of any other suitable method of bulk material removal (e.g., laser cutting, water jet cutting, etc, etching, etc.).

In the first variation, the substrate can be composed of a semiconducting material (e.g., highly-doped single crystal silicon, quartz, gallium arsenide), a conducting material (e.g., gold, steel, platinum), and/or an insulating material (e.g., glass, ceramic). In some variations, the substrate 130 can comprise a combination of materials (e.g., as in a composite, as in an alloy). In a specific example, the substrate is composed of P-type, boron-doped, <100> orientation silicon with a resistivity of 0.005-0.01 ohm-cm, a thickness from 500-1500 µm, and a TTV of <10 µm, with a first surface side polish. In variations of the specific example, the substrate 130 can be composed of silicon with any other suitable type, doping, miller index orientation, resistivity, thickness, TTV, and/or polish.

Figure 6A:
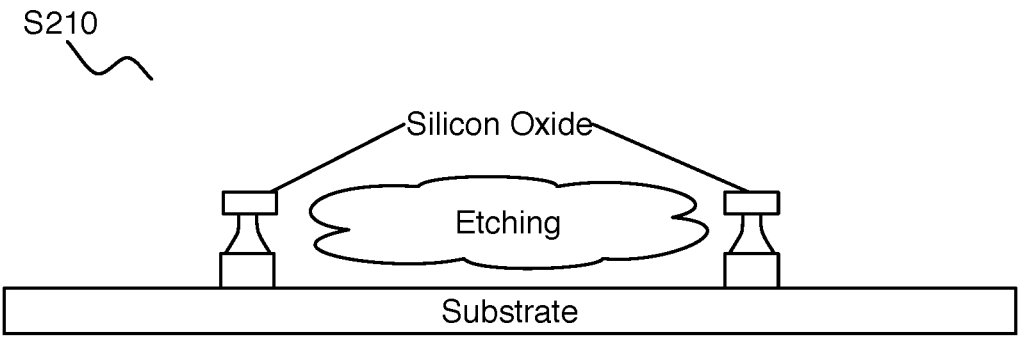
FIGS. 6A and 6B depict variations of forming a filament substrate.

As shown in FIG. 6A, in a second variation, Block S210 comprises creating a substrate, applying a photoresist to the substrate, and etching the substrate to form the filament substrate. The second variation of Block S210 preferably defines an array of sharp protrusions, wherein each sharp protrusion has a base end, coupled to the substrate, a sharp tip end, and a rotational axis of symmetry defined between the base end and the sharp tip end. In variations, each sharp protrusion can be defined by an inwardly tapering profile, such that sharp protrusion has a base end defined by a first width (or diameter), and widens from the base end for at least a portion of the length of the sharp protrusion. However, the second variation of Block S210 can include forming protrusions, defined by any other suitable profile, at the substrate. The second variation can comprise performing a Bosch process, a deep-reactive ion etching (DRIE) process, any suitable etch (e.g., a potassium hydroxide etch), or any other suitable process to form the filament substrate. In a specific example of the second variation, the substrate comprises a P++ and/or silicon-doped silicon wafer with an oxide pad, a negative photoresist is applied in a uniform pattern to the oxide pad, and potassium hydroxide anisotropic etching is used to form the filament substrate. In further detail regarding the specific example, the substrate is composed of P-type, boron-doped, <100> orientation silicon with a resistivity of 0.005-0.01 ohm-cm, a thickness from 500-1500 µm, and a TTV of <10 µm, with a first surface side polish. In variations of the specific example, the substrate 130 can be composed of silicon with any other suitable type, doping, miller index orientation, resistivity, thickness, TTV, and/or polish. In alternative examples of the second variation, Block S210 can comprise using any appropriate semiconductor substrate, applying a positive photoresist and/or a negative photoresist to the semiconductor substrate, applying the photoresist in a non-uniform pattern, and/or using any appropriate etching method (e.g., anisotropic, isotropic) to form the filament substrate.

Figure 6B:
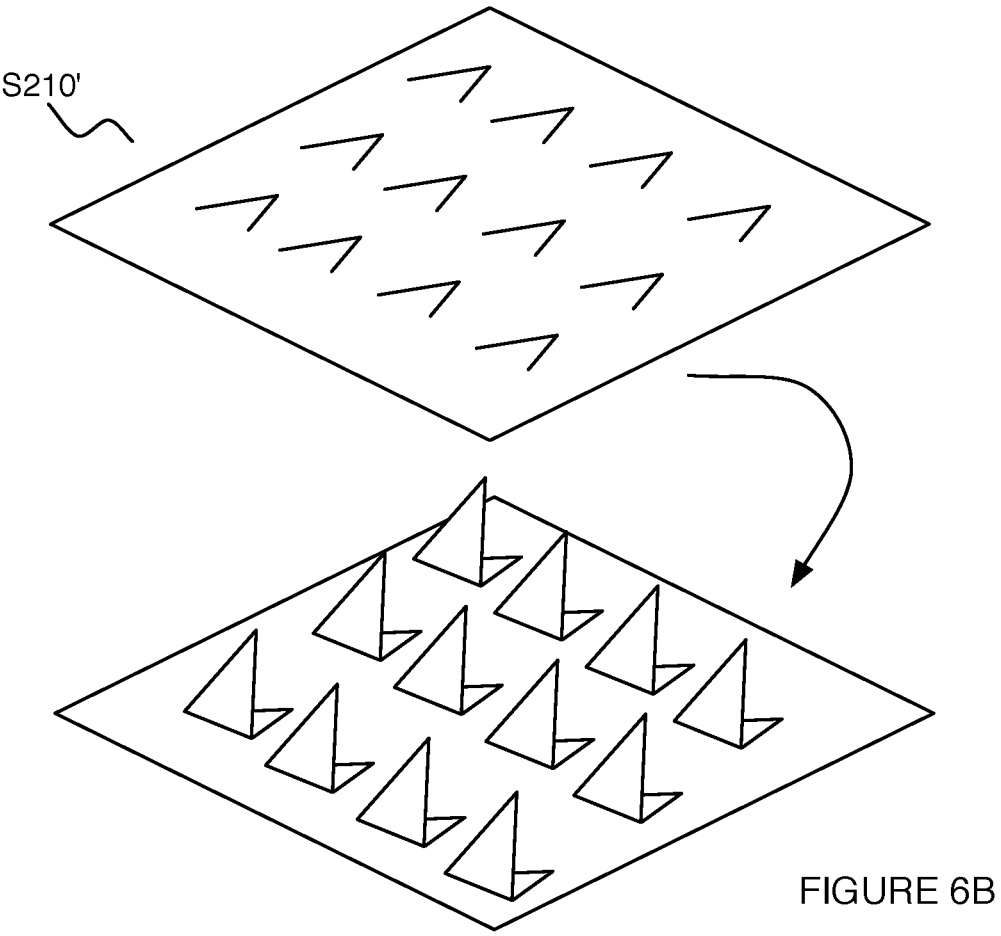

In a third variation, as shown in FIG. 6B, Block S210' comprises etching an array into a ductile substrate and deforming the array to form an array of protrusions, thus forming a filament substrate. In a specific example of the third variation, an array of v-shaped features is laser-etched into a ductile steel substrate, and each v-shaped feature in the array of v-shaped features is then deformed outward from the steel substrate by 90° to form an array of v-shaped filament protrusions. Alternative examples of the third variation can include etching the array using any appropriate method (e.g., punching, die-cutting, water cutting), etching any appropriate array feature (e.g., any pointed feature), and deforming the array in any appropriate manner (e.g., by any angular amount for each or all array features) to form the array of protrusions. In alternative variations, the filament substrate can be formed by any other suitable method (e.g., molding, laser cutting, stamping, 3D printing, etc.).

Block S220 recites applying a conductive layer to the filament substrate S220, and functions to form a conductive "active" region to facilitate signal transmission upon detection of an analyte by a filament of the microsensor. Preferably, Block S220 comprises coupling a conductive layer to the sharp tip of each columnar protrusion in the array of columnar protrusions formed, for example, in variations of Block S211a and S211b. In variations, coupling the conductive layer can include electroplating a conductive material or alloy of a conductive material (e.g., nickel, silver, iridium, tungsten, titanium, titanium nitride, aluminum, cadmium, chromium, molybdenum, lead, gold, platinum, etc.) to the sharp tip of each columnar protrusion. Block S220 can additionally or alternatively comprise metalizing the filament substrate by sputtering a layer of any appropriate conductive material (e.g., gold, platinum, doped silicon, nickel, silver, iridium, tungsten, titanium, titanium nitride, aluminum, cadmium, chromium, molybdenum, lead, etc.) onto the filament substrate. In still other variations, however, Block S220 can alternatively or additionally comprise metalizing the filament substrate by plating or evaporating a layer of any appropriate conductive material onto the filament substrate, or by applying the conductive material (e.g., nickel, gold, platinum, doped silicon, tungsten, iridium, titanium nitride) in any other suitable manner. In addition to applying the conductive material to the sharp tips of the array of protrusions defined in Block S210, Block S220 can include coupling a second conductive layer to a second surface of the substrate (e.g., a surface of the substrate directly opposing the array of protrusions), in order to define a second conductive surface of the substrate to facilitate electrical coupling for signal transmission (e.g., upon detection of an analyte).

Preferably, Block S220 comprises applying the conductive layer to the filament substrate in a substantially uniform manner (e.g., as an even layer with substantially uniform thickness); however, Block S220 can alternatively comprise applying the conductive layer to the filament substrate in a non-uniform manner, such that some regions of the conductive layer are thicker than others. Furthermore, Block S220 can include application of multiple layers of one or more conductive materials, in order to form a conductive layer comprising multiple layers of materials. In variations involving sputtering or evaporation, the filament substrate can be translated or rotated while being sputter coated or evaporation coated to facilitate uniform deposition of the conductive layer. In variations involving plating to apply the conductive layer, the plating can be applied using chemical or electrochemical plating, to any appropriate thickness.

Block S230 recites defining an active region and a non-active region of the filament with an insulating layer, and functions to form at least one insulating region of a filament of the microsensor. Preferably, Block S230 comprises applying an insulating layer to a portion of the filament substrate/conductive layer assembly, in a manner wherein at least one region of the conductive layer is not covered (e.g., uncovered, exposed, unsheathed) with the insulating layer (thus forming the active and non-active regions of the filament). Block S230 can be performed using vapor deposition (e.g., chemical vapor deposition) of an oxide, thermal oxide growth, spin coating, spray coating, or any other appropriate method of depositing a localized layer of an insulting material. Preferably, the insulating layer is composed of an insulating oxide; however, the insulating layer can additionally or alternatively include an insulating polymer (e.g., polyimide, cyanate ester) that is chemical and heat resistant and/or any appropriate material (e.g., thermally grown silicon oxide, chemical vapor deposited oxides, titanium oxide, tantalum oxide, other oxides, chemical vapor deposited nitrides, other nitrides, paralene, etc.) that is configured to insulate a portion of the filament substrate/conductive layer assembly. Furthermore, in Block S230, the insulating layer can be grown or deposited uniformly or non-uniformly over desired surfaces (e.g., all exposed surfaces, active regions formed through bulk material removal, active regions defined by chemical etching, plasma etching, high energy etching, any other suitable type of etching, etc.).

In a first example of Block S230, an oxide layer can be deposited at exposed surfaces of the substrate (e.g., all exposed surfaces of the substrate, of substrate cores of protrusions, cut surfaces, etc.), using a chemical vapor deposition (CVD) process. In the first example, the CVD process allows for controlled coupling of an oxide layer to the substrate surface at which the filaments are formed (e.g., without resulting in oxide generation or formation at a backside surface of the substrate). As such, in relation to patterning of metal pads at another surface of the substrate, wherein the metal pads facilitate signal transduction from the microsensor, the first example can provide a more efficient process that does not require subsequent removal of oxide from the backside surface of the substrate. The oxide layer preferably couples to the exposed surfaces of the substrate in a manner that discourages unbonding or removal of the oxide material during subsequent Blocks of the method 200. In variations of the first example, the oxide layer can be formed at the substrate or coupled to the substrate using any one or more of: an atmospheric pressure CVD (APCVD) process, a low pressure CVD (LPCVD) process, an ultrahigh vacuum CVD (UHCVD) process, a aerosol assisted CVD (AACVD) process, a direct liquid injection CVD (DLICVD) process, a microwave plasma-assisted (MPCVD) process, a plasma-enhanced CVD (PECVD) process, an atomic layer CVD (ALCVD) process, a combustion CVD (CCVD) process, a hot filament CVD (HFCVD) process, a photo-initiated CVD (PICVD) process, and any other suitable CVD process, in order to define an oxide layer of any other suitable thickness.

In a second example of Block S230, an oxide layer can be formed at exposed surfaces of the substrate (e.g., all exposed surfaces of the substrate, of substrate cores of protrusions, cut surfaces, etc.), by a thermal oxide growth process. The oxide layer preferably couples to the exposed surfaces of the substrate in a manner that discourages unbonding or removal of the oxide material during subsequent Blocks of the method 200. In the first example, the oxide layer is formed by way of a thermal oxide growth process at 900-1050 C for 1-2 hours, in order to induce 0.1-10 μm thick thermal oxide growth. In variations of the first example, however, the oxide layer can be formed at the substrate or coupled to the substrate using a thermal process defined by any suitable temperature parameters, for any suitable duration of time, in order to define an oxide layer of any other suitable thickness.

Figure 7A:
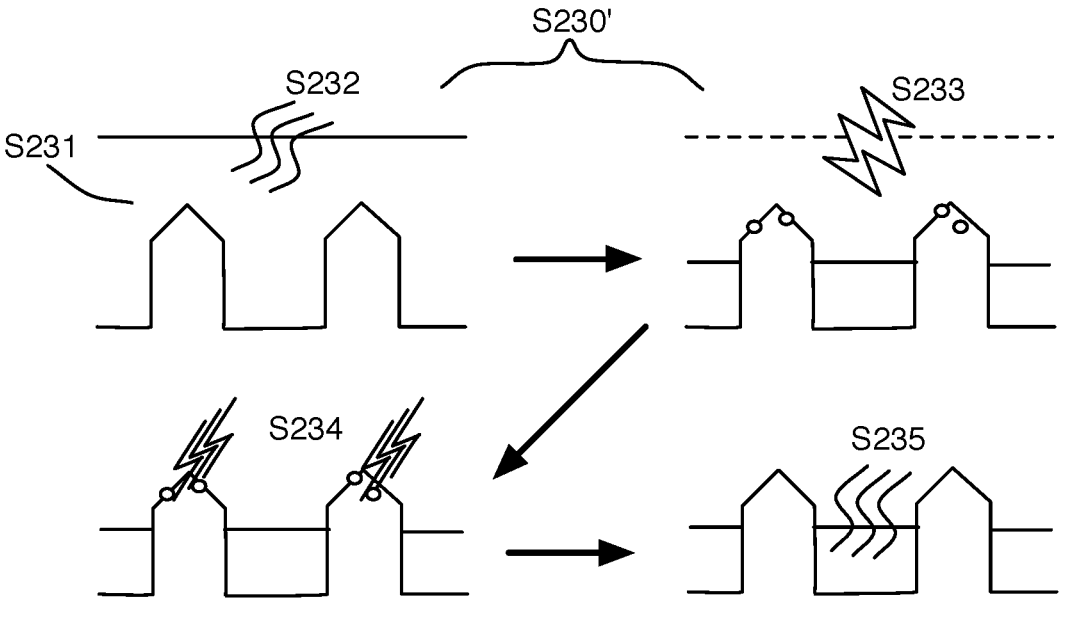
FIGS. 7A-7D depict variations of defining an active region and a non-active region of the filament with an insulating layer.

In a third example of Block S230', as shown in FIG. 7A, an insulating polymer (e.g., polyimide, cyanate ester) can be deposited over the substrate or substrate/conductive layer subassembly S231. The insulator may then be soft-baked S232 to facilitate selective removal of the insulating polymer. In the second example, the tip regions of the filaments can then be exposed by selectively dissolving or etching the soft-baked insulating polymer S233, and the tip regions of the filaments can be cleaned S234 (e.g., using a plasma-etching process). Finally, the filament assembly comprising active and non-active regions can be hard-baked to cure the insulating polymer S235. In a variation of the second example, the insulating polymer can be photosensitive, such that Block S232 uses a photolithographic process to selectively expose areas above filaments or between filaments (to increase solubility), and so that the a positive photolithographic process or a negative photolithographic process can be used to define the active/non-active regions. Additionally, Block S235 can use a photo-crosslinking process to cure the insulating polymer.

Figure 7B:
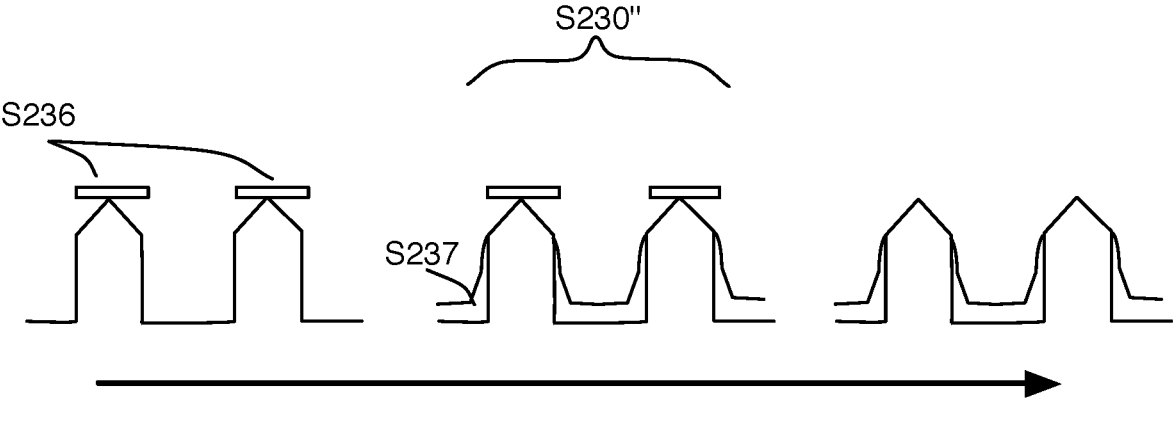

In a fourth example of Block S230", as shown in FIG. 7B, a set of oxide caps coupled to filament tips (produced, for instance, during a Bosch or DRIE process) can be used to shield the filament tips S236, and a dielectric or other insulating material can be applied to define active and non-active regions S237. The insulating material in the third example can be applied using a line of sight deposition method, preferably at an angle, such that the insulating material is applied only to specific regions (e.g., between filament tips). The line of sight deposition method can be an evaporation method (e.g., to deposit an insulating polymer), or can additionally or alternatively be a sputtering method (e.g., sputtering of titanium or tantalum), followed by oxidation to produce the insulating layer. The filament assembly can then be passivated (e.g., during a DRIE process) and the oxide caps can be removed (e.g., pinched off) to expose the active regions.

Figure 7C:
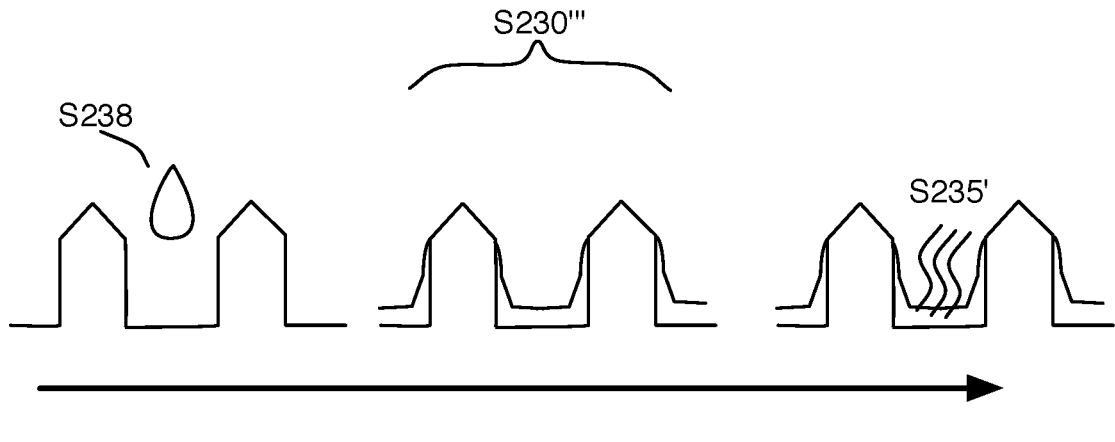

In a fifth example of Block S230''', as shown in FIG. 7C, the insulating material can be fluidly deposited between filament structures (e.g., by inkjet printing, silk screening, dispensing) S238. The insulating material can be a molten polymer (e.g., nylon), or can be a polymer that is in solution form (e.g., silicon, polyurethane, polyimide) that is subsequently cured S235' (e.g., baking, photo-crosslinking) to remove solvent and form the active and non-active regions.

Figure 7D:
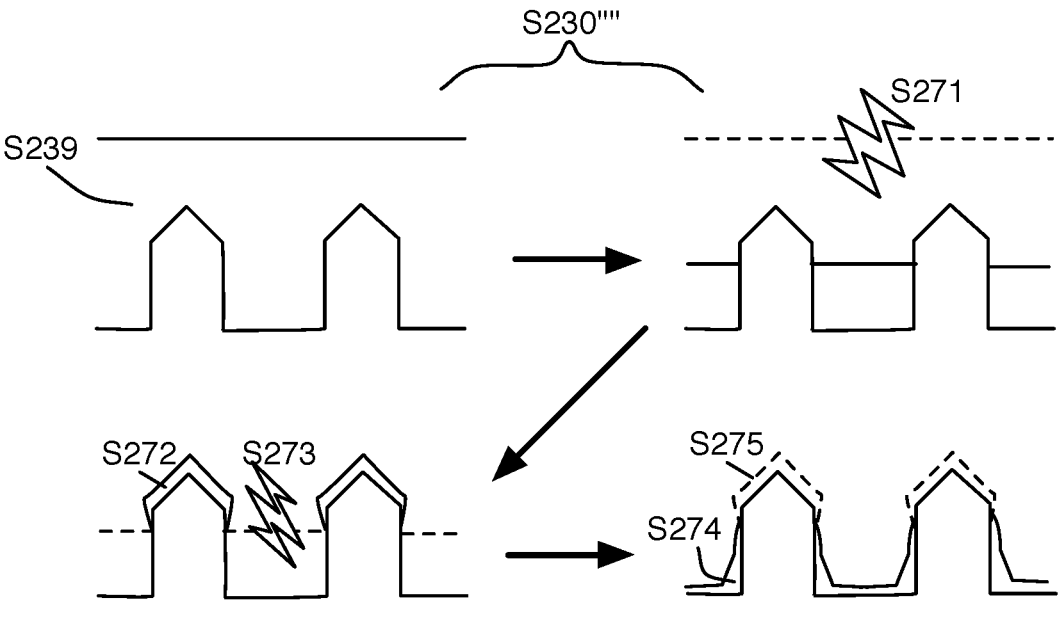

In a sixth example of Block S230'''', as shown in FIG. 7D, a photoresist can be applied to the substrate or substrate/ conductive layer subassembly S239, and then etched away to expose filament tips S271. The tips may then be protected with a intermediary layer (e.g., metal or soluble insulator) S272, the photoresist can be removed by further etching S273, and then non-tip regions may then be passivated to form non-active insulating regions S274. Finally, the intermediary layer can be removed to define the active regions S275. Block S230 can alternatively comprise any other suitable method of defining an active region and a non-active region of the filament with an insulating layer.

In a seventh example of Block S230''''', the insulating material (e.g., parylene) used to define the active regions and non-active regions can also be deposited by a chemical vapor deposition (CVD) process. In this example, the tips of the filaments can be protected with a temporary protective layer (e.g., by covering each needle tip photolithographically using photoresist or applying a small droplet of photoresist or other soluble polymer to each filament tip). Then, the insulating material (e.g., parylene) can be deposited in a CVD process to conformally coat the unprotected filament areas. After deposition of the insulating material, the temporary protective layer can be removed (e.g., by using an appropriate solvent), to form the active and the non-active regions.

In variations of the method 200, Blocks S220 and S230 can be performed in any suitable order, in relation to defining an array of sharp tips in variations of Block S210, and in order to define active/non-active regions. In a first variation of the method 200, forming an array of columnar protrusions S211b at the substrate can be performed prior to forming an insulating layer at exposed surfaces of the substrate in Block S230. Then, the insulating layer can be selectively removed, as desired, from surfaces of the substrate (e.g., at a surface of the substrate directly opposing that of the array of columnar protrusions). After selective removal of the insulating layer, an array of sharp protrusions can be formed at distal ends of the array of columnar protrusions in variations of the method including Block S211a, and the conductive layer can be coupled to all regions of the substrate not covered by the insulating layer, thereby coupling the conductive layer to at least the tip regions of the array of protrusions in a variation of Block S220. As such, active region/non-active regions can be defined through bulk material removal (e.g., cutting, dicing) or any other suitable process including one or more of: selective chemical etching, plasma etching, high energy etching, and any other suitable etching method.

In a second variation, which can extend from the first variation, the method 200 can include Blocks S210, S220, and S230, and further include using a sacrificial layer to selectively isolate a region of the substrate during processing S283, in order to facilitate processing of the conductive layer and/or the insulating layer in Blocks S220 and S230, respectively. The sacrificial layer can include an aluminum layer (e.g., sputtered aluminum, evaporated aluminum, etc.). The sacrificial layer can additionally or alternatively include a nitride material (e.g., 1000-2500 Å thick nitride), an oxide material, a carbide material, a salt, a sugar, a polymer (e.g., polyethylene glycol), and/or any other suitable material that does not deteriorate during subsequent processing steps. Furthermore, the sacrificial layer can be bioabsorbable and/ or porous to facilitate biocompatibility and/or processing. In one example, forming an array of sharp protrusions S211a can be performed prior to coupling a conductive layer to the array of sharp protrusions and any other desired surface of the substrate (e.g., a surface directly opposing that of the array of sharp protrusions), as in variations of Block S230, followed by coupling of a sacrificial layer to all surfaces of the substrate with the conductive layer.

Figure 8A:
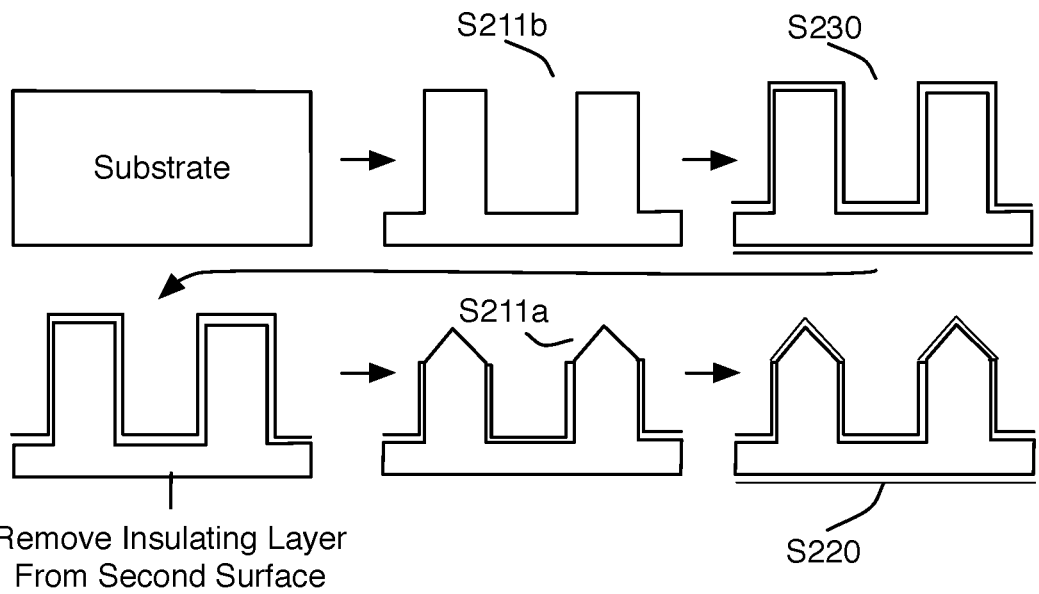
FIGS. 8A-8E depict variations of a portion of an embodiment of a method for an on-body microsensor for biomonitoring.
Figure 8B:
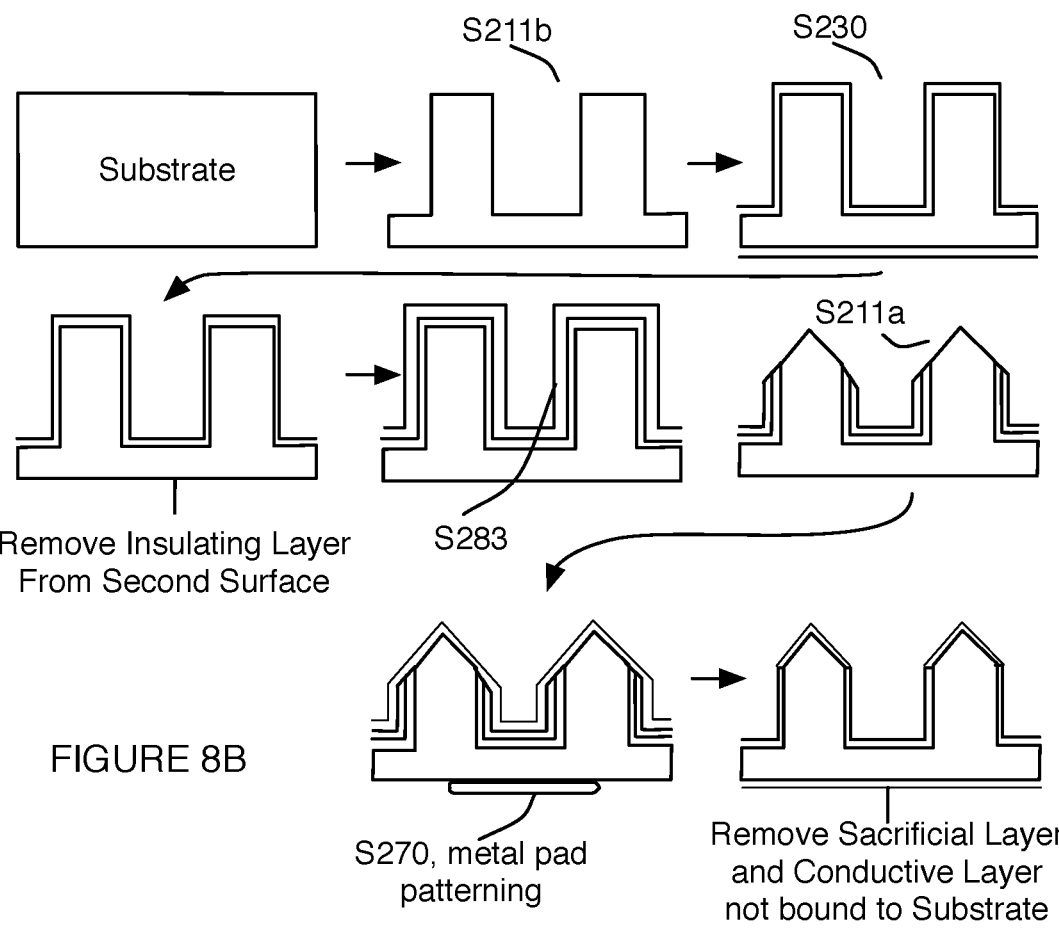

In an example, as shown in FIG. 8B, an array of columnar protrusions can be formed as in Block S211b by removing material between the array of sharp protrusions or columnar protrusions, after which an insulating layer can be generated at all exposed surfaces of the substrate (e.g., by thermal oxide growth), as in Block S230. Then, an angled blade of a dicing saw can be passed across the array of columnar protrusions a desired number of times and/or with a desired number of orientations to produce the array of sharp protrusions, wherein the substrate material is exposed at the tip regions of the sharp protrusions through the insulating layer and the sacrificial layer. The sacrificial layer S283 can then be removed (e.g., by etching) prior to subsequent processing steps (e.g., coupling of a conductive layer to the sharp tips of the array of sharp protrusions. Additionally or alternatively, the thermal oxide at the side of substrate opposing the array of protrusions can be removed (e.g., by etching), followed by subsequent processing steps (e.g., patterning of metal pads at the "backside" of the substrate, in order to facilitate coupling of the microsensor to an electronics subsystem, as described in more detail below.

Figure 10:
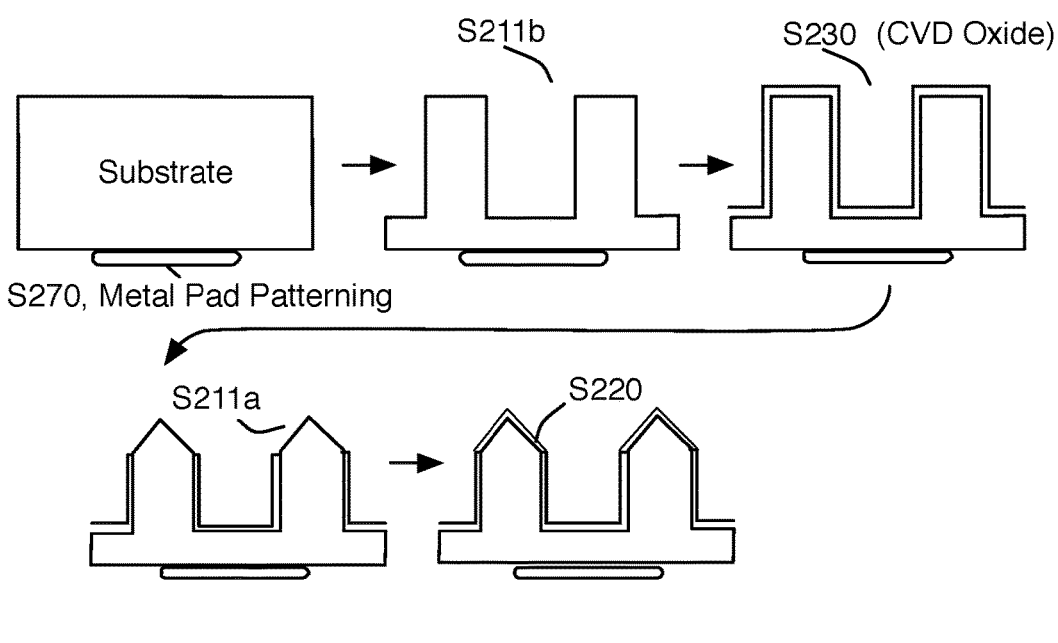
FIG. 10 depicts a portion of an embodiment of a method for an on-body microsensor for biomonitoring.

In another example, as shown in FIG. 10A, an array of columnar protrusions can be formed as in Block S211b by removing material of the substrate with a dicing saw, after which an insulating layer can be coupled to exposed surfaces of the array of columnar protrusions (e.g., by CVD of an oxide), as in Block S230. Then, an angled blade of a dicing saw can be passed across the array of columnar protrusions a desired number of times and/or with a desired number of orientations to produce the array of sharp protrusions from the array of columnar protrusions, wherein the substrate material is exposed at the tip regions of the sharp protrusions through the insulating layer. This example can further include patterning of metal pads at the "backside" of the substrate, in order to facilitate coupling of the microsensor to an electronics subsystem, as described in more detail below, wherein patterning of the metal pads can occur without requiring removal of oxide from the backside, due to the frontside CVD process.

In another example, forming an array of sharp protrusions S211a can be performed prior to coupling of a sacrificial layer, as in Block S283, at all surfaces of the substrate intended to be coupled to a conductive layer. Material can then be removed between the array of sharp protrusions to form an array of columnar protrusions, as in Block S211b, after which an insulating layer can be formed at all exposed surfaces of the substrate, as in Block S230. Then, the sacrificial layer can be removed and the conductive layer can be coupled to all regions of the substrate formerly occupied by the sacrificial layer, as in variations of Block S220. In other examples, coupling of the sacrificial layer can be omitted or performed at any suitable stage of the method 200, specific examples of which are described in further detail below.

As shown in FIG. 8A, in a first specific example of processing the substrate, the conductive layer, and the sensing layer in Blocks S210, S220, and S230, material is removed from a first surface of the substrate, thereby forming an array of columnar protrusions as in Block S211b. Removing material in the first specific example is performed by way of a non-angled blade of a dicing saw in order to remove material from the first surface of the substrate to a desired depth of ~400 μm, a width of 100 μm, and a gap of 500 μm, at a cutting rate of 2-3 mm/s. In the first specific example, the dicing saw is configured to form the array of columnar protrusions through adjacent cuts in a first direction, followed by adjacent cuts in a second direction orthogonal to the first direction, thereby forming a 2-dimensional array of columnar protrusions. In the first specific example, the substrate is composed of P-type, boron-doped, <100> orientation silicon with a resistivity of 0.005-0.01 ohm-cm, a thickness from 500-1500 μm, a total thickness variation (TTV) of <10 μm, and with a first surface side polish. Subsequent to formation of the array of columnar protrusions, an insulating layer of ~1 μm oxide is formed at all exposed surfaces of the substrate, as in Block S240, by inducing thermal oxide growth at 900-1050 C for 1-2 hours. Then, the insulating layer is removed from a second surface of the substrate, directly opposing the surface of the substrate at which the columnar protrusions were formed, by way of a directed plasma etch. Subsequently, an array of sharp protrusions is formed, as in Block S211a, by removing material from the distal end of each columnar protrusion. Forming an array of sharp protrusions is performed by way of a 500 μm, 60-degree angled blade of a dicing saw configured to cut 2-facet tips at a rate of 4 mm/s. Similar to forming the array of columnar protrusions, the dicing saw is configured to form the array of sharp protrusions through adjacent cuts in a first direction, followed by adjacent cuts in a second direction orthogonal to the first direction, thereby forming a 2-dimensional array of sharp protrusions (i.e., sharp tips). Lastly, in the first specific example, a conductive layer is coupled to the array of sharp protrusions and the second surface of the substrate by electroplating (e.g., of nickel, of gold, and/or of platinum), as in Block S220.

As shown in FIG. 8B, in a second specific example of processing the substrate, the conductive layer, and the sensing layer in Blocks S210, S220, and S230, material is removed from a first surface of the substrate, thereby forming an array of columnar protrusions as in Block S211b. Removing material in the second specific example is performed by way of a non-angled blade of a dicing saw in order to remove material from the first surface of the substrate to a desired depth of ~400 μm, a width of 100 μm, and a gap of 500 μm, at a cutting rate of 2-3 mm/s. In the second specific example, the dicing saw is configured to form the array of columnar protrusions through adjacent cuts in a first direction, followed by adjacent cuts in a second direction orthogonal to the first direction, thereby forming a 2-dimensional array of columnar protrusions. In the second specific example, the substrate is composed of P-type, boron-doped, <100> orientation silicon with a resistivity of 0.005-0.01 ohm-cm, a thickness from 500-1500 μm, a total thickness variation (TTV) of <10 μm, and with a first surface side polish. Subsequent to formation of the array of columnar protrusions, an insulating layer of ~1 μm oxide is formed at all exposed surfaces of the substrate, as in Block S230, by inducing thermal oxide growth at 900-1050 C for 1-2 hours. Then, the insulating layer is removed from a second surface of the substrate, directly opposing the surface of the substrate at which the columnar protrusions were formed, by way of a directed plasma etch. Following removal of the insulating layer from the second surface, a sacrificial layer is coupled to all surfaces of the substrate still coupled to the insulating layer. Subsequently, an array of sharp protrusions is formed, as in Block S211a, by removing material from the distal end of each columnar protrusion. Forming an array of sharp protrusions is performed by way of a 500 μm, 60-degree angled blade of a dicing saw configured to cut 2-facet tips at a rate of 4 mm/s. Similar to forming the array of columnar protrusions, the dicing saw is configured to form the array of sharp protrusions through adjacent cuts in a first direction, followed by adjacent cuts in a second direction orthogonal to the first direction, thereby forming a 2-dimensional array of sharp protrusions (i.e., sharp tips). Lastly, in the second specific example, a conductive layer is coupled to the array of sharp protrusions and the second surface of the substrate by electroplating (e.g., of nickel, of gold, and/or of platinum) as in Block S220, followed by removal of the sacrificial layer from the insulating layer. The sacrificial layer, in the second specific example, thus functions to facilitate isolation of the conductive layer to desired surfaces, such that the conductive layer does not substantially overlap with the insulating layer in an undesired manner.

Figures 8C, 8D:
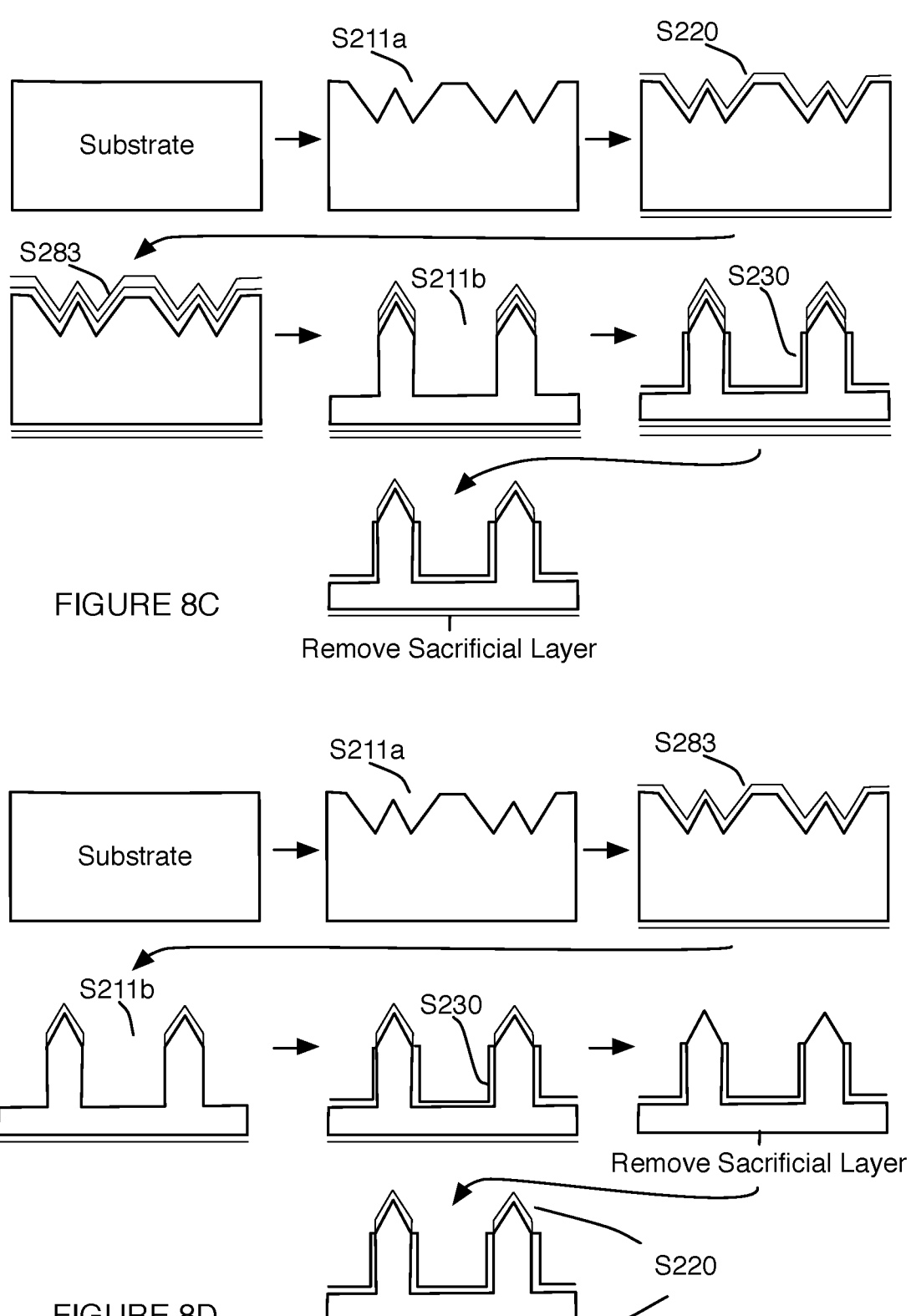

As shown in FIG. 8C, in a third specific example of processing the substrate, the conductive layer, and the sensing layer in Blocks S210, S220, and S230, material is removed from a first surface of the substrate to form an array of sharp protrusions (e.g., sharp tips), as in Block S211a. Forming an array of sharp protrusions is performed by way of a 500 μm, 60-degree angled blade of a dicing saw configured to cut 2-facet tips at a rate of 4 mm/s. In the third specific example, the dicing saw is configured to form the array of sharp protrusions through adjacent cuts in a first direction, followed by adjacent cuts in a second direction orthogonal to the first direction, thereby forming a 2-dimensional array of sharp protrusions. In the third specific example, the substrate is composed of P-type, boron-doped, <100> orientation silicon with a resistivity of 0.005-0.01 ohm-cm, a thickness from 500-1500 μm, a total thickness variation (TTV) of <10 μm, and with a first surface side polish. Subsequent to forming the array of sharp protrusions, a conductive layer is coupled to the array of sharp protrusions and a second surface of the substrate, directly opposed to the array of sharp protrusions, as in Block S220, by depositing 1000 Å of platinum, 1000 Å of iridium, 1000 Å of tungsten, and 100 Å of titanium nitride at the desired surfaces. In variations of the third specific example, the conductive layer can include: a 1000 Å thick platinum layer and a 100 Å thick titanium layer, a 1000 Å thick platinum layer and a 100 Å thick titanium nitride layer, a 1000 Å thick iridium layer and a 100 Å thick titanium nitride layer, or a 1000 Å thick tungsten layer. A sacrificial layer comprising a 1000-2500 Å thick layer of nitride is then coupled to the conductive layer, as in Block S283, and material is removed from the substrate between each sharp protrusion in the array of sharp protrusions, thereby forming an array of columnar protrusions coupled to the array of sharp protrusions, as in Block S211b. Forming the array of columnar protrusions is performed by way of a non-angled blade of a dicing saw in order to remove material from the first surface of the substrate to a desired depth of ~400 μm, a width of 100 μm, and a gap of 500 μm, at a cutting rate of 2-3 mm/s. In the third specific example, the dicing saw is configured to form the array of columnar protrusions through adjacent cuts in a first direction, followed by adjacent cuts in a second direction orthogonal to the first direction, thereby forming a 2-dimensional array of columnar protrusions. An insulating layer is formed at all exposed surfaces (e.g., cut surfaces without conductive layer or sacrificial layer) of the substrate, as in Block S230, by inducing thermal oxide growth to a thickness of 1 μm at 900-1050 C for 1-2 hours. Then, the sacrificial layer is removed by a directed plasma etch.

As shown in FIG. 8D, in a fourth specific example of processing the substrate, the conductive layer, and the sensing layer in Blocks S210, S220, and S230, material is removed from a first surface of the substrate to form an array of sharp protrusions (e.g., sharp tips), as in Block S211a. Forming an array of sharp protrusions is performed by way of a 500 μm, 60-degree angled blade of a dicing saw configured to cut 2-facet tips at a rate of 4 mm/s. In the fourth specific example, the dicing saw is configured to form the array of sharp protrusions through adjacent cuts in a first direction, followed by adjacent cuts in a second direction orthogonal to the first direction, thereby forming a 2-dimensional array of sharp protrusions. In the fourth specific example, the substrate is composed of P-type, boron-doped, <100> orientation silicon with a resistivity of 0.005-0.01 ohm-cm, a thickness from 500-1500 μm, a total thickness variation (TTV) of <10 μm, and with a first surface side polish. A sacrificial layer comprising a 1000-2500 Å thick layer of nitride is then coupled to the array of sharp protrusions and to a second surface of the substrate directly opposing the array of sharp protrusions, as in Block S283, and material is removed from the substrate between each sharp protrusion in the array of sharp protrusions, thereby forming an array of columnar protrusions coupled to the array of sharp protrusions, as in Block S211b. Forming the array of columnar protrusions is performed by way of a non-angled blade of a dicing saw in order to remove material from the first surface of the substrate to a desired depth of ~400 μm, a width of 100 μm, and a gap of 500 μm, at a cutting rate of 2-3 mm/s. In the fourth specific example, the dicing saw is configured to form the array of columnar protrusions through adjacent cuts in a first direction, followed by adjacent cuts in a second direction orthogonal to the first direction, thereby forming a 2-dimensional array of columnar protrusions. An insulating layer is formed at all exposed surfaces (e.g., cut surfaces without sacrificial layer) of the substrate, as in Block S230, by inducing thermal oxide growth to a thickness of 1 μm at 900-1050 C for 1-2 hours. Then, the sacrificial layer is removed by a directed plasma etch. Subsequent to removal of the sacrificial layer, a conductive layer is coupled to the array of sharp protrusions and a second surface of the substrate, directly opposed to the array of sharp protrusions, as in Block S220, by depositing 1000 Å of platinum, 1000 Å of iridium, 1000 Å of tungsten, and 100 Å of titanium nitride at the desired surfaces. In variations of the fourth specific example, the conductive layer can include: a 1000 Å thick platinum layer and a 100 Å thick titanium layer, a 1000 Å thick platinum layer and a 100 Å thick titanium nitride layer, a 1000 Å thick iridium layer and a 100 Å thick titanium nitride layer, or a 1000 Å thick tungsten layer. Other variations of the fourth specific example can include electroplating of any suitable metal (e.g., nickel, gold, platinum).

Figure 8E:
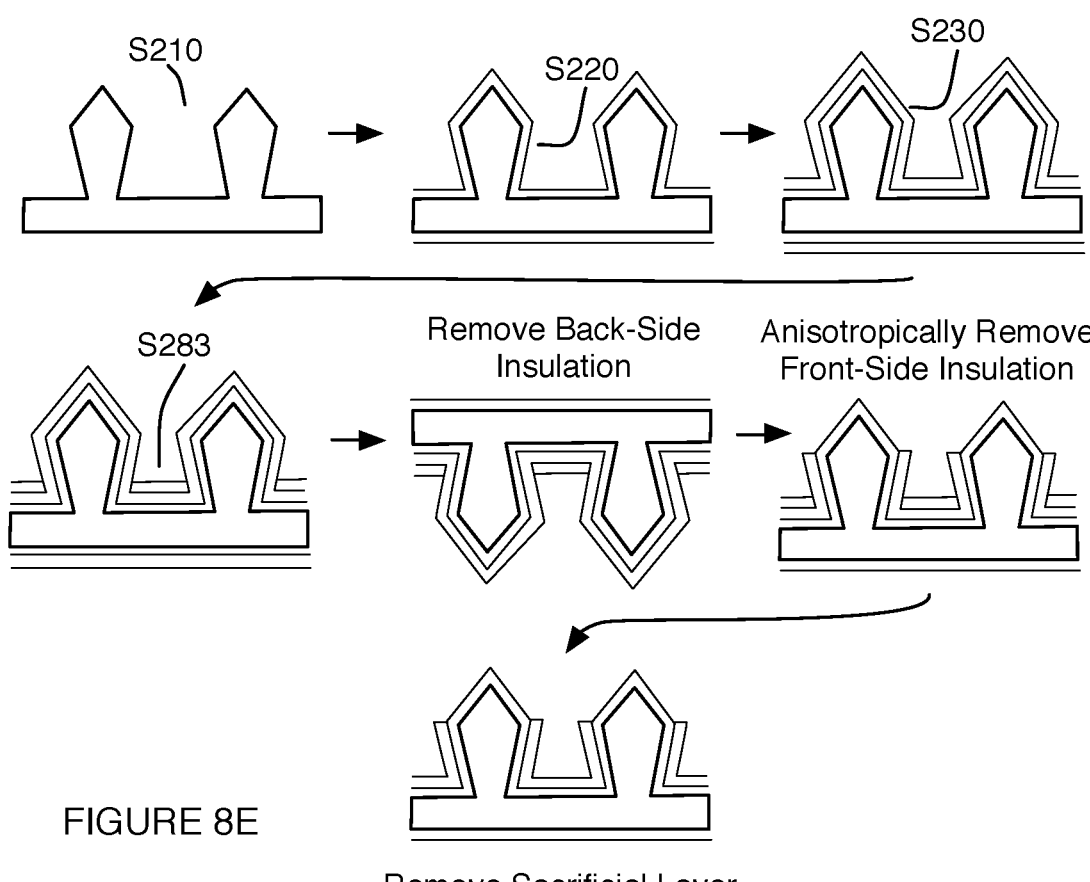

As shown in FIG. 8E, in a fifth specific example of processing the substrate, the conductive layer, and the sensing layer in Blocks S210, S220, and S230, an array of sharp protrusions, with a tapered profile (i.e., tapering from a tip end toward a base end coupled to the substrate), is formed at a first surface of a substrate by a DRIE process, as in Block S210. A conductive layer is then coupled to all exposed surfaces of the substrate, as in Block S220 by depositing 1000 Å of platinum, 1000 Å of iridium, 1000 Å of tungsten, and 100 Å of titanium nitride at the exposed surfaces. In variations of the fifth specific example, the conductive layer can include: a 1000 Å thick platinum layer and a 100 Å thick titanium layer, a 1000 Å thick platinum layer and a 100 Å thick titanium nitride layer, a 1000 Å thick iridium layer and a 100 Å thick titanium nitride layer, or a 1000 Å thick tungsten layer. Other variations of the fifth specific example can include electroplating of any suitable metal (e.g., nickel, gold, platinum) to form the conductive layer. Subsequent to formation of the conductive layer, an insulating layer comprising a nitride material is then coupled to the conductive layer, as in Block S230, and a sacrificial layer is then coupled to the insulating layer, as in Block S283, at regions of the substrate between the base ends of the array of sharp protrusions. In the fifth specific example, the sacrificial layer is applied by way of a spin photoresist. Subsequently, the insulating layer is removed from the tip regions of the array of sharp protrusions and from a second surface of the substrate, directly opposed to the array of sharp protrusions, by way of an anisotropically directed plasma field. Lastly, the sacrificial layer is removed (e.g., by etching).

In other examples of the method 200, processing the substrate, the conductive layer, and the sensing layer in Blocks S210, S220, and S230 can be performed according to any other suitable process and in any other suitable order. Furthermore, in variations of the described processes, any suitable number of blades, cutting surfaces, other tool for removal of material can be used to increase processing speed/efficiency.

2.2 Manufacturing Method-Sensing Layer and Selective Layer Processing

Block S240 recites applying a sensing layer to at least the conductive layer, and functions to form a filament coating that enables transduction of an ionic concentration to an electronic voltage. Preferably, the sensing layer is applied selectively to the filament substrate/conductive layer/insulating layer assembly at regions where the conductive layer is exposed (e.g., only at active regions); however, the sensing layer can alternatively be applied to the entire filament substrate/conductive layer/insulating layer assembly. In variations wherein the sensing layer is applied selectively to the filament substrate/conductive layer/insulating layer assembly, Block S240 can comprise electrodeposition, lithography, inkjet printing, screen printing, dip coating, spray coating, or any other appropriate method for applying the sensing layer selectively. In variations wherein the sensing layer is applied to the entire filament substrate/conductive layer/insulating layer assembly, Block S240 can comprise glazing, spin coating, spray coating, or any method of applying a polymer coating in a non-selective manner.

Preferably, the sensing layer is composed of a material with reversible redox reaction behavior, as previously described. In one example, the sensing layer can comprise a nitrogen-containing polymer, such as polypyrrole or polyaniline. The sensing layer can additionally or alternatively be composed of any appropriate conductive material. In another example, the sensing layer can additionally or alternatively comprise a protein or peptide serving as a complementary molecule to an analyte, such as glucose oxidase for glucose sensing or valinomycin for potassium sensing. In variations of this example, the sensing layer can comprise amino acids (e.g., lysine) and/or polymer chains of subsequently associated amino acids (e.g., poly-lysine). In providing a protein distribution, an amino acid distribution, a polymer chain distribution, and/or any other particle distribution at the sensing layer in Block S240, the distribution can be uniform or non-uniform (e.g., concentrated in desired regions, concentrated at a surface, etc.), homogenous or heterogeneous, and generated in any suitable manner.

Figure 9:
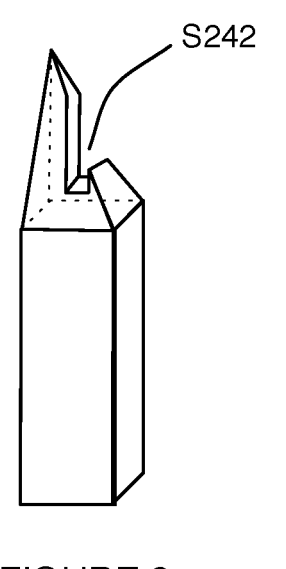
FIG. 9 depicts a portion of an embodiment of a method for an on-body microsensor for biomonitoring.

In some variations, Block S240 can include forming a notch at least at one sharp protrusion (i.e., sharp tip) of the array of sharp protrusions S242 formed, as in Block S211a. The notch, as shown in FIG. 9, can be used as a pocket to isolate the sensing layer, and can additionally or alternatively be filled with any other suitable functional material. In one such variation, the notch can be filled with a protective material that functions to protect the sensing layer during insertion or during a period of contact with the user's body fluid. In another variation, the notch can be filled with a "calibration material" configured to provide or release an analyte according to a known profile (e.g., release profile, concentration, degradation profile, etc.). In another variation, the notch can be filled with a therapeutic substance to facilitate delivery of the therapeutic substance to a user in a drug delivery application. The notch can be formed in alignment with a sharp tip of a filament, or can alternatively be form in misalignment with a warp tip of a filament. Variations of Block S240 can entirely omit forming the notch, or can including providing a notch for any other suitable purpose.

Some variations of the method can further include Block S245, which recites: coupling an intermediate selective layer to the conductive layer defined in Block S220. In a variation wherein another layer (e.g., an intermediate active layer that facilitates transduction, as described in Section 1 above) is coupled superficial to the conductive layer defined in Block S220, the method can include a variation of Block S245 as Block S246, which recites: providing an intermediate selective layer able to transmit a signal to the conductive layer, and coupling the sensing layer defined in Block S240 to the intermediate selective layer. Blocks S245 and S246 function to provide an additional selective layer to facilitate detection of an analyte (e.g., glucose) in a selective manner. In some variations, Blocks S245 and S246 can include applying a polymer superficial to the conductive layer, and polymerizing the polymer to set the intermediate selective layer. In specific examples of Blocks S245 and S246, the intermediate selective layer can include phenylenediamine for glucose sensing, which is electropolymerized to set the intermediate selective layer. Other variations of these specific examples can include polymerization of any other suitable material in any other suitable manner (e.g., chemical polymerization, heat polymerization, photopolymerization, etc.). Other variations of Blocks S245 and S246 can alternatively include providing a non-polymeric material as the intermediate sensing layer, which can be processed in any other suitable manner.

Block S250 recites forming a selective layer, and functions to form a layer configured to facilitate sensing of specific target analytes. Preferably, Block S250 comprises forming a selective layer comprising a polymer matrix with a distribution of complementary molecules S252 to at least one target analyte characterizing a user's body chemistry. Block S252 preferably comprises forming a homogenous mixture of the polymer matrix material (e.g., in either a solution or gel phase) with the distribution of complementary molecules, but can alternatively comprise forming a heterogeneous mixture of the polymer matrix material with the distribution of complementary molecules. Alternatively, Block S252 can be replaced by Block S254, which comprises depositing a layer of a polymer matrix and depositing the distribution of complementary molecules, onto the assembly produced after Block S240, in any order. In still another alternative, Block S250, S252 and/or Block S254 can be performed prior to one or more of Blocks S220, S230, and S240, such that a selective layer is deposited at different times and/or different locations during processing of the microsensor. In one such example, in a sensor for glucose detection applications, Block S250 is performed subsequent to Block S220 (e.g., immediately over the conductive layer). In another example, with a conductive substrate, Block S250 can be performed subsequent to Block S210 (e.g., a selective layer can be deposited onto a tip region of the conductive substrate). Forming a selective layer comprising a polymer matrix can further comprise forming a selective layer with a polymer matrix and a plasticizer, in embodiments wherein a flexible polymer matrix is desired for Block S250. In one specific example, the polymer matrix comprises polyvinyl chloride (PVC) with a plasticizer to increase flexibility; however, in other variations, the polymer matrix can be composed of any other suitable polymer (e.g., amine-decorated polymer, polyethylene, polytetrafluoroethylene, urethane, polyurethane, phenylenediamine, ortho-phenylenediamine, protein matrices, amino acid matrices, etc.), with or without a plasticizer, and configured to contain a distribution of complementary molecules. Again, in one example, the distribution of complementary molecules comprises glucose oxidase molecules for glucose sensing, and in another example, the distribution of complementary molecules comprises valinomycin molecules for potassium sensing. Block S250 can be performed by spin coating a polymer matrix-complementary molecule mixture with or without a plasticizer, by drop casting a polymer matrix-complementary molecule mixture with or without a plasticizer, or by any appropriate method. Additionally, spin coating, dip coating, spray coating, drop casting, electrodeposition, electroplating, or any other suitable method of application can be performed in stages, such that the selective layer is characterized by a tunable thickness. The tunable thickness preferably governs a rate at which complementary molecules bind to target analytes (e.g., diffusion rate), and governs the amount (e.g., concentration or total amount) of complementary molecules within the selective layer and/or defines a molecular size cut-off.

In some variations, in particular, variations of manufacturing a microsensor for glucose sensing, the method 200 can additionally or alternatively include Block S256, which recites: providing a stabilizing layer configured to stabilize the sensing layer. Block S256 preferably functions to stabilize a glucose oxidase sensing layer, in manufacturing a microsensor for glucose sensing; however, Block S256 can additionally or alternatively function to stabilize the sensing layer for any other suitable application. In some variations, Block S256 can include providing a polymer superficial to the sensing layer, and polymerizing the polymer to set the intermediate selective layer. In specific examples of Block S256, the stabilizing layer can include phenylenediamine for glucose sensing, which is electropolymerized to set the stabilizing layer. Other variations of this specific example can include polymerization of any other suitable material in any other suitable manner (e.g., chemical polymerization, heat polymerization, photopolymerization, etc.). Other variations of Block S256 can alternatively include providing a non-polymeric material as the intermediate sensing layer, which can be processed in any other suitable manner.

In some variations, in particular, variations of manufacturing a microsensor for glucose sensing, the method 200 can additionally or alternatively include Block S258, which recites: providing an intermediate protective layer superficial to the sensing layer. Block S258 preferably functions to form a layer that provides intermediate protection and/or block transport of undesired species. In some variations, Block S258 can include providing a polymer superficial to the sensing layer, including at least one functional compound configured to provide a protective barrier. In examples, the polymer of the intermediate protective layer can include any one or more of: teflon, chlorinated polymer, nafion, polyethylene glycol, and any other suitable polymer, and can include functional compounds including one or more of: lipids, charged chemical species that block transport of charged species, surfactants, and any other suitable compound. Other variations of Block S258 can alternatively include providing a non-polymeric material as the intermediate protective layer, which can be processed in any other suitable manner.

2.3 Manufacturing Method-Singulation/Separation of Individual Microsensor Units

In some variations, as shown in FIG. 4 the method 200 can include Block S260, which recites: separating the microsensor unit from an adjacent microsensor unit. Block S260 functions to facilitate mass manufacturing of microsensor units using a single substrate, whereby one or more of the steps associated with conductive layer application, active and non-active region defining, sensing layer application, selective layer application, and any other suitable layer processing can be performed for multiple microsensor units simultaneously, followed by separation/singulation of individual microsensor units. As such, separation/singulation of the individual microsensor units in Block S260 can be performed after Block S250, or can be performed at any other suitable stage of the method 200. Additionally or alternatively, separation/singulation of microsensor units can be performed in multiple stages (e.g., a scoring stage following by a separation stage along one or more score lines), in relation to Blocks S210, S220, S230, S240, and S250, as described in further detail below.

In a first variation, Block S260 can include, with a dicing saw, separating the microsensor unit from the adjacent microsensor unit, wherein separation initiates from the side of the microsensor units at which the protrusions are formed. In this variation, dicing can occur at any suitable speed, with or without wet cutting techniques (e.g., with a fluid drip) in order to cleanly and precisely separate adjacent microsensor units. In a specific example of this variation, Block S260 can include dicing adjacent microsensor units with a wet-cutting technique with phosphate buffered saline (PBS). In another specific example, wherein a rectangular array of microsensor units is being generated, Block S260 can include passing the dicing saw between adjacent microsensor units along a first direction (any suitable number of instances), and then passing the dicing saw between adjacent microsensor units from a second direction that is perpendicular to the first direction (any suitable number of instances) to form singular microsensor units from the array of microsensor units.

In a second variation, Block S260 can include, with a dicing saw, separating the microsensor unit from the adjacent microsensor unit, wherein separation initiates from the side of the microsensor units opposite the side at which the protrusions are formed (e.g., in a stealth backside dicing process). In this variation, dicing can occur at any suitable speed, with or without wet cutting techniques (e.g., with a fluid drip) in order to cleanly and precisely separate adjacent microsensor units. Furthermore, in this variation, any suitable support structure can be positioned at the "front-side" of the microsensor unit array, in order to prevent undesired breakage/fracturing during a "backside" dicing process. In a specific example of this variation, Block S260 can include dicing adjacent microsensor units with a stealth back-side dicing process, whereby the front-side of the microsensor units is supported with a plate structure that has recesses or openings for any processed surfaces (e.g., protrusions, active regions, non-active regions, sensing layers, selective layers, etc.), and or recesses to accommodate blade passage through the regions between adjacent microsensor units. In another specific example, wherein a rectangular array of microsensor units is being generated, Block S260 can include passing the dicing saw between adjacent microsensor units along a first direction (any suitable number of instances), and then passing the dicing saw between adjacent microsensor units from a second direction that is perpendicular to the first direction (any suitable number of instances) to form singular microsensor units from the array of microsensor units.

In a third variation, Block S260 can include implementing a scoring and breaking process to separate the microsensor unit from an adjacent microsensor unit. In this variation, scoring can be performed at the side of the microsensor units at which the protrusions are formed. Additionally or alternatively, scoring can be performed at the side of the microsensor units opposite the side at which the protrusions are formed. In examples, scoring can be performed with a diamond tipped scoring instrument (e.g., diamond scribe) or any other suitable instrument that can create a suitable scoring line into the surface of the substrate (or any other suitable portion of the microsensor unit). In examples, breaking can be performing using one or more of: a tapping process, a temperature modulating process (e.g., a heating process), an impact process, a bending process, and any other suitable process.

In a fourth variation, Block S260 can include implementing a trenching and separation process to separate the microsensor unit from an adjacent microsensor unit. In this variation, trenching can be performed at the side of the microsensor units at which the protrusions are formed. Additionally or alternatively, trenching can be performed at the side of the microsensor units opposite the side at which the protrusions are formed. In examples, trenching can be performed with a narrower blade of a dicing saw or any other suitable instrument that can create a suitable trench at the surface of the substrate (or any other suitable portion of the microsensor unit). In examples, breaking can be performing using one or more of: a tapping process, a temperature modulating process (e.g., a heating process), an impact process, a bending process, and any other suitable process.

2.4 Manufacturing Method-Additional or Alternative Steps

As noted above and shown in FIG. 4, some variations of the method 200 can include Block S270, which recites: patterning at least one metal pad at a surface of the substrate away from the array of sharp protrusions. Block S270 functions to provide a contact pad that can interface with electronics in communication with the microsensor during use, such that the microsensor can communicate signals to the electronics subsystem/computing system for further processing and/or analysis. In Block S270, patterning the metal pad(s) can comprise a multi-step process, wherein metal (e.g., one or more of gold, aluminum, platinum, titanium, etc.) is applied to the surface of the substrate, and then portions of the applied metal are then removed to pattern the contact pads onto the substrate. In a first example, Block S270 can include an evaporation and lift-off process to pattern the metal pad(s) onto the substrate, and in a second example, Block S270 can include a sputter and etching process to pattern the metal pad(s) onto the substrate. However, Block S270 can additionally or alternatively include any other suitable step(s).

Preferably, Block S270 includes patterning of the metal pad(s) onto a substrate surface directly opposing the substrate surface at which the protrusions are located, in a "backside" patterning process. However, Block S270 can additionally or alternatively include patterning of the metal pad(s) at any other suitable substrate region that allows for signal transduction, through the metal pads, to an electronics subsystem. For instance, some variations of Block S270 can include patterning metal contacts at another surface (e.g., at a front or top side of the substrate) conducive to a wire bonding process.

Block S270 can be implemented at any suitable stage of processing, in relation to other Blocks of the method 200. For instance, in a first example, Block S270 can be implemented prior to CVD of an oxide layer as an insulating layer at exposed protrusion surfaces (an example of which is shown in FIG. 10A), wherein the controlled deposition of the oxide insulating layer at the "frontside" with the protrusions allows for patterning of the metal pads at the "backside" without damage (e.g., during the deposition process, in association with any etching processes). Alternatively in relation to generation of an insulating layer by way of thermal oxide growth, Block S270 can be implemented after the oxide has been removed from regions intended for metal pad coupling.

Some variations of the method 200 can further include Block S280, which recites: performing at least one washing stage and at least one drying stage, which functions to remove salts and/or any other undesired components from layers of the microsensor during or after processing. Block S280 can also function to increase the longevity of polymers used in the microsensor, such that the shelf life of the microsensor (e.g., in packaging) is increase. Block S280 can include use of one or more of: de-ionized water, low chloride buffers, any other suitable buffers, and any other suitable washing agent. Furthermore, Block S280 can include any suitable drying process (e.g., baking, air-drying, etc.). Block S280 can be implemented multiple times throughout processing of layers of the microsensor (e.g., with each polymer layer); however, Block S280 can alternatively be implemented only once during processing of the microsensor (e.g., with a final washing and drying stage prior to packaging).

2.5 Multi-Electrode Probe Array and Manufacturing

As indicated above, variations of the sensor system 100 described in Section 1 above can be configured with multiple conductive regions and insulating regions that isolate portions of the conductive regions, in order to generate subregions of the sensor units that can be used to sense different analytes. For instance, each filament of an array of filaments can have multiple conductive layers coupled to sensing layers and isolated by respective insulating layers, in order to generate a filament configuration that can be used to sense multiple analytes, without interference across different sensing layers. Such configurations are described in Section 2.5.1 below. Analogously, as indicated above variations of the method 200 described above can additionally or alternatively be configured to generate multiple conductive layers and/or multiple sensing layers, isolated by insulating regions to define active regions, as described in Section 2.5.2 below.

2.5.1 Multi-Electrode Probe

Figure 11A:
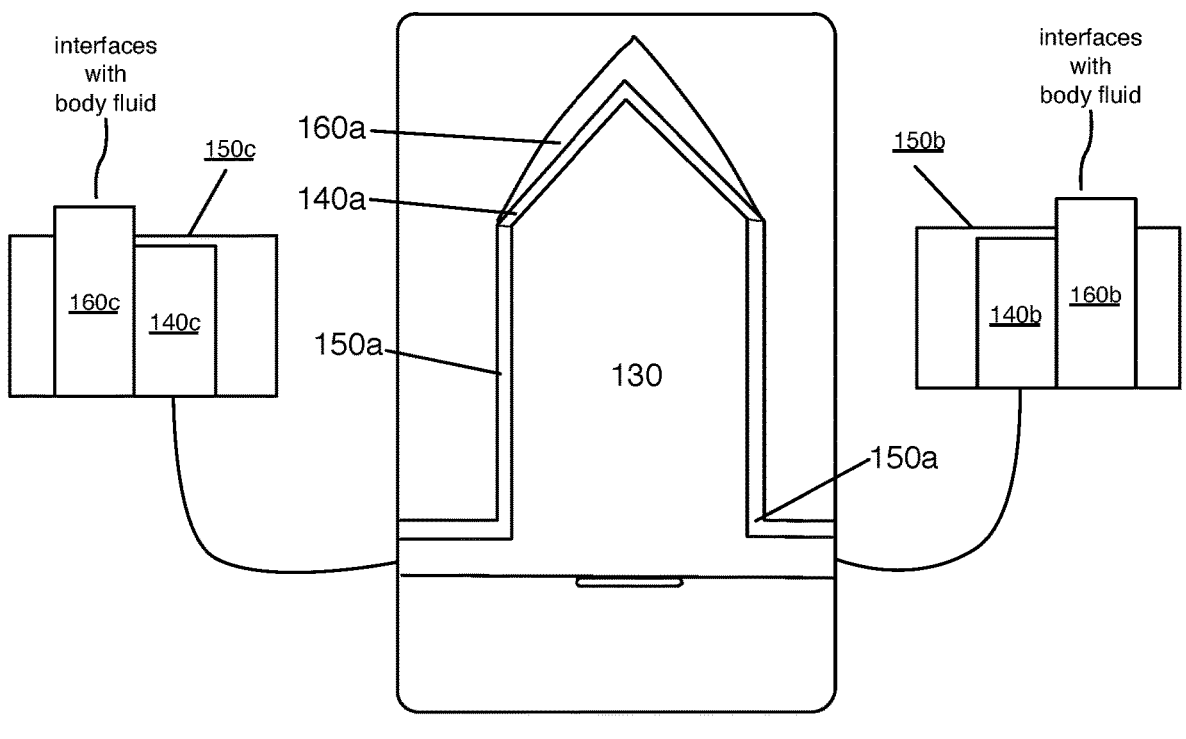
FIGS. 11A-11B depict embodiments and variations of a multi-electrode microsensor for biomonitoring.

As shown in FIG. 11A, a multi-electrode sensor 300 can include: a substrate 130, an array of filaments 110, each filament 120 including: a substrate core including a columnar protrusion having a base end coupled to the substrate 130 and a distal portion operable to provide access to a body fluid of the user during operation of the sensor; a first conductive layer 140a isolated to the distal portion of the substrate core and away from the base end as a first active region operable to transmit electronic signals generated upon detection of a first analyte within the body fluid; a first insulating layer 150a surrounding the substrate core and exposing a portion of the first conductive layer at the distal portion, thereby isolating the first conductive layer 140a to the distal portion of the substrate and from other regions of the sensor; and a first sensing layer 160a in communication with the first active region defined by the first conductive layer and operable for sensing of the first analyte.

As shown in FIG. 11A, the multi-electrode sensor can additionally or alternatively include additional conductive layers, insulating layers, and sensing regions configured to facilitate detection of signals attributed to interactions with additional analytes of interest. As such, in some variations, the sensor can include: a second conductive layer 140b; a second isolating layer 150b exposing a portion of the second conductive layer 140b, thereby defining a second active region operable to transmit electronic signals generated upon detection of a second analyte within the body fluid; a second sensing material volume 160b in communication with the second active region defined by the second conductive layer and operable for sensing of the second analyte; a third conductive layer 140c; a third isolating layer 150c exposing a portion of the third conductive layer 140c, thereby defining a third active region operable to transmit electronic signals generated upon detection of a third analyte within the body fluid; a third sensing material volume 160c in communication with the third active region defined by the third conductive layer and operable for sensing of the third analyte.

Furthermore, while three conductive layers, three insulating/isolating layers, and three sensing regions are discussed, variations of the multi-electrode sensor can additionally or alternatively include any other suitable number of conductive layers, insulating/isolating layers, and/or sensing regions for detecting any other suitable number of analytes of interest. Additionally or alternatively, the analytes associated with each of the active regions can be the same analyte (e.g., for sensor redundancy), or can alternatively be different analytes, as described in Sections 1 and 2 above.

Embodiments, variations, and examples of the substrate 130, the substrate core, the first conductive layer 140a, the first insulating layer 150a, and the first sensing layer 160a can be configured according to the embodiments, variations, and examples described in Section 1 above.

As indicated above, the multi-electrode sensor 300 can additionally or alternatively include one or more of: a second conductive layer 140b, a second isolating layer 150b, a second sensing material volume 160*b*, a third conductive layer 140*c*; a third isolating layer 150*c*, and a third sensing material volume 160*c*.

Similar to the conductive layer 140 described above, the second conductive layer 140*b* functions to provide a conductive "active" region to facilitate signal transmission upon detection of a second analyte by a filament. The second conductive layer 140*b* can comprise a layer of a single material, or can alternatively comprise multiple materials (e.g., multiple layers of one or more materials). In variations, the second conductive layer 140*b* can include any one or more of: a platinum-based material, an iridium-based material, a tungsten-based material, a titanium-based material, a gold-based material, a nickel-based material, and any other suitable conductive or semiconducting material (e.g., silicon, doped silicon). Furthermore, the layer(s) of the second conductive layer 140*b* can be defined by any suitable thickness that allows signal transmission upon detection of the second analyte.

Figure 13A:
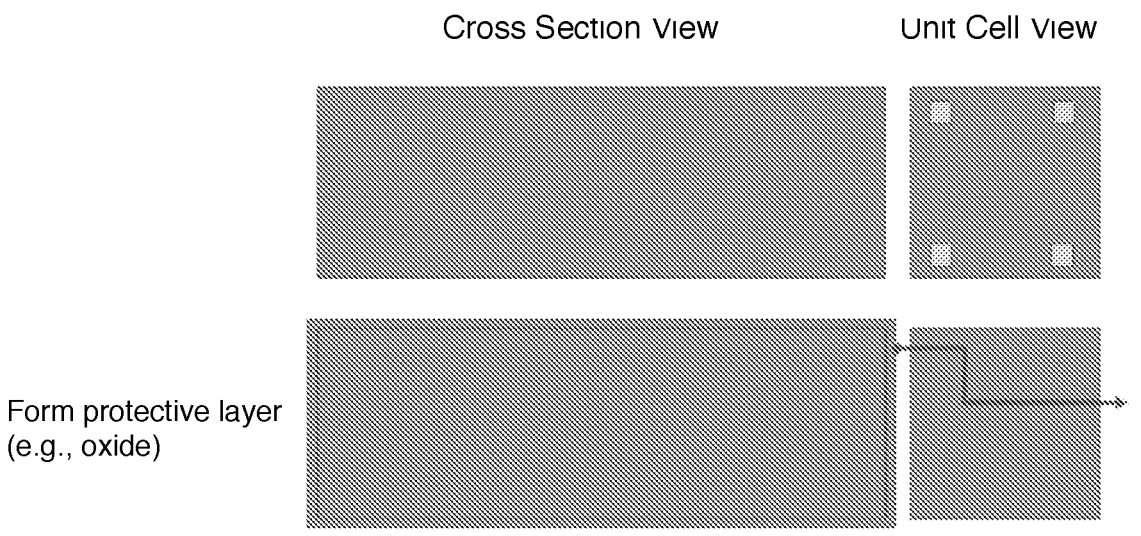
FIGS. 13A-13C depict a variation of a portion of a method for manufacturing of a multi-electrode microsensor for biomonitoring.
Figure 13B:
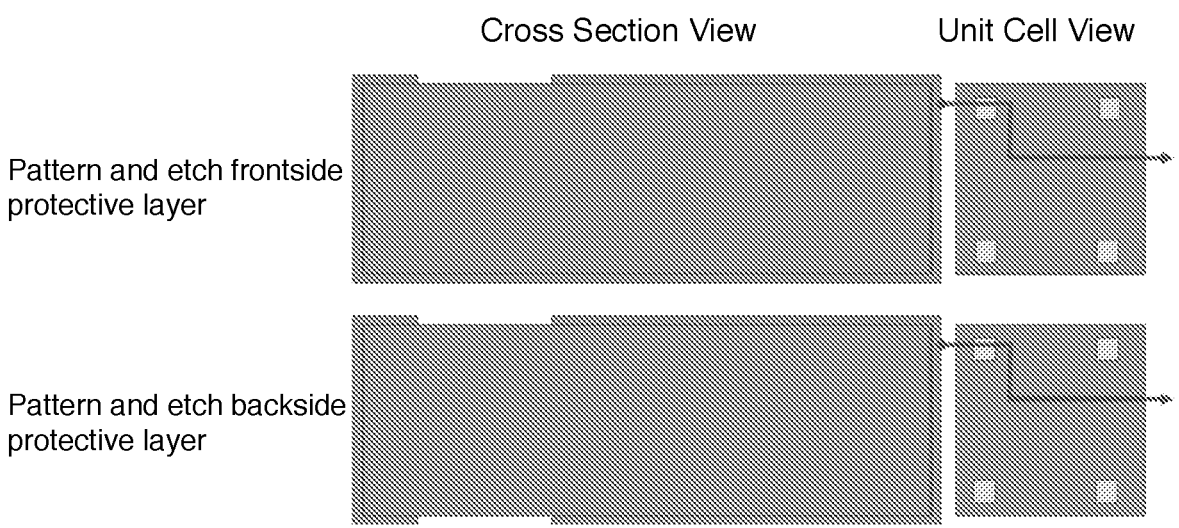

Preferably, the second conductive layer 140*b* is coupled to the substrate and isolated from other conductive layers 140, 140*c*, etc. by insulating or isolating layers, in order to prevent signal interference and to provide specificity in relation to detection of different analytes. In one variation, as shown in FIG. 13B, the second conductive layer 140*b* surrounds (e.g., sheathes) the first insulating layer 150*a*, and is separated from the first insulating layer 150*b* by the second isolating layer 150*b*, which also surround the first insulating layer 150*a*. However, the second conductive layer 140*b* can alternatively cover any other suitable portion of the substrate 130 and/or any other suitable layer of the multi-electrode sensor 300.

The second isolating layer 150*b* functions to isolate the second conductive layer 140*b* from other regions of the sensor 300. The second isolating layer 150*b* is preferably composed of a polymer, and can be printed, deposited, grown, dip-coated, or applied to the sensor assembly in any suitable manner. In an example, the second isolating layer 150*b* is composed of a poly-silicon material; however, variations of the second isolating layer 150*b* can additionally or alternatively be composed of any other suitable polymer, any other suitable insulating material, and/or any other suitable material. For instance, variations of the second isolating layer 150*b* can be composed of materials used for the insulating layer 150 described in Section 1 above.

Figure 11B:
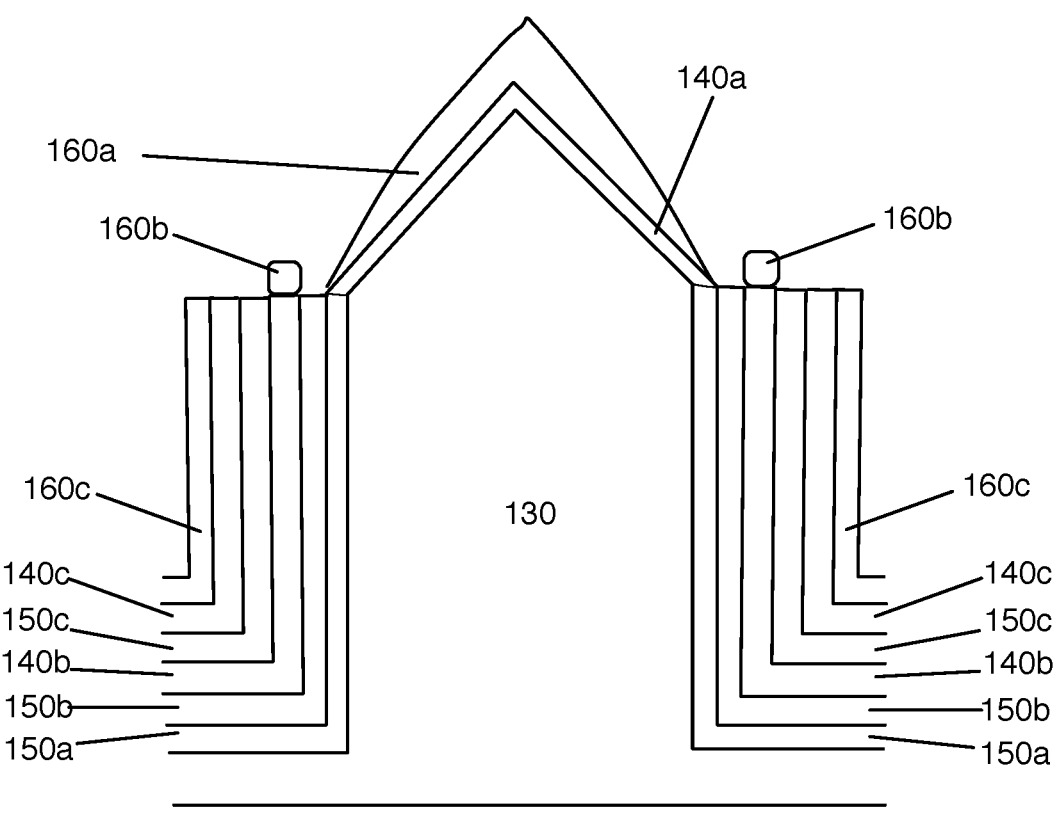

Preferably, as shown in FIG. 11B, the second isolating layer 150*b* separates the second conductive layer 140*b* from the first insulating layer 150*a*, and in a specific example, the second isoalting layer is directly coupled to the first insulating layer 150*a* and surrounds (e.g., sheathes) the first insulating layer 150*a*, thereby separating the second conductive layer 140*b* from the first insulating layer 150*a*. However, the second isolating layer 150*b* can alternatively cover any other suitable portion of the substrate 130 and/or any other suitable layer of the multi-electrode sensor 300.

The second sensing material volume 160*b* functions to enable transduction of a concentration of the second analyte to an electronic voltage, in order to enable measurement of features associated with the content of the second analyte within the body fluid of the user. The second sensing material volume 160*b* can also function to prevent unwanted signal artifacts due to fluxes (e.g., oxygen fluxes) in a user's body fluids. Furthermore, the second sensing material volume 160*b* can also enable transduction of a molecular species concentration through a current, capacitance, or resistance change. Preferably, the second sensing material volume 160*b* is a conductive material with reversible redox reaction behavior, such that detection of increased concentrations followed by decreased concentrations (or visa versa) can be enabled by the sensing material volume 160*b*. Additionally, the second sensing material volume 160*b* is preferably an appropriately bio-safe, anti-inflammatory, and anti-microbial material. The second sensing material volume 160*b* can be a polymer, such as polypyrrole or polyaniline, Additionally or alternatively, the second sensing material volume can include molecules that facilitate analyte detection. In variations, the sensing layer can include one or more amine-decorated polymer materials. For instance, in examples, the amine-decorated polymer material(s) implemented can include one or more of: tyramine, phenylenediamine, lysine, and any other suitable amine-decorated polymer.

Preferably, as shown in FIG. 11B, the second sensing material volume 160*b* is directly coupled to portions of the second conductive layer 140*b* exposed through the other layers (e.g., the second isolating layer 150*b*). In a specific example, wherein the second conductive layer 140*b* forms a sheath (or tube) about the second isolating layer 150*b*, the second sensing material volume can form a ring of material coupled to the exposed annular surface of the second conductive layer 140*b*. However, the second sensing material layer 160*b* can alternatively cover any other suitable portion of the second conductive layer 140*b*, the substrate 130 and/or any other suitable layer of the multi-electrode sensor 300.

Similar to the conductive layer 140 and the second conductive layer 140*b* described above, the third conductive layer 140*c* functions to provide a conductive "active" region to facilitate signal transmission upon detection of a third analyte by a filament. The third conductive layer 140*c* can comprise a layer of a single material, or can alternatively comprise multiple materials (e.g., multiple layers of one or more materials). In variations, the second conductive layer 140*b* can include any one or more of: a platinum-based material, an iridium-based material, a tungsten-based material, a titanium-based material, a gold-based material, a nickel-based material, and any other suitable conductive or semiconducting material (e.g., silicon, doped silicon). Furthermore, the layer(s) of the third conductive layer 140*c* can be defined by any suitable thickness that allows signal transmission upon detection of the second analyte.

Preferably, the third conductive layer 140*c* is coupled to the substrate and isolated from other conductive layers 140, 140*b*, etc. by insulating or isolating layers, in order to prevent signal interference and to provide specificity in relation to detection of different analytes. In one variation, as shown in FIG. 13B, the third conductive layer 140*b* surrounds (e.g., sheathes) the substrate core, and is separated from the second conductive layer 140*b* by the third isolating layer 150*c* described below. However, the third conductive layer 140*c* can alternatively cover any other suitable portion of the substrate 130 and/or any other suitable layer of the multi-electrode sensor 300.

The third isolating layer 150*c* functions to isolate the third conductive layer 140*c* from other regions of the sensor 300. The third isolating layer 150*c* is preferably composed of a polymer, and can be printed, deposited, grown, dip-coated, or applied to the sensor assembly in any suitable manner. In an example, the third isolating layer 150*c* is composed of a poly-silicon material; however, variations of the third isolating layer 150*c* can additionally or alternatively be composed of any other suitable polymer, any other suitable insulating material, and/or any other suitable material. For instance, variations of the third isolating layer 150*c* can be composed of materials used for the insulating layer 150 described in Section 1 above.

Preferably, as shown in FIG. 11B, the third isolating layer 150C separates the third conductive layer 140c from the second conductive layer 140b, and in a specific example, the third isolating layer is directly coupled to the second conductive layer 140b and surrounds (e.g., sheathes) the second conductive layer 140, thereby separating the second conductive layer 140b from the first insulating layer 150a and exposing an annular surface of the second conductive layer 140b, to which the second sensing material region 160b can be coupled, as described above. However, the third isolating layer 150c can alternatively cover any other suitable portion of the substrate 130 and/or any other suitable layer of the multi-electrode sensor 300.

The third sensing material volume 160c functions to enable transduction of a concentration of the third analyte to an electronic voltage, in order to enable measurement of features associated with the content of the third analyte within the body fluid of the user. The third sensing material volume 160c can also function to prevent unwanted signal artifacts due to fluxes (e.g., oxygen fluxes) in a user's body fluids. Furthermore, the third sensing material volume 160c can also enable transduction of a molecular species concentration through a current, capacitance, or resistance change. Preferably, the third sensing material volume 160b is a conductive material with reversible redox reaction behavior, such that detection of increased concentrations followed by decreased concentrations (or visa versa) can be enabled by the sensing material volume 160c. Additionally, the third sensing material volume 160c is preferably an appropriately bio-safe, anti-inflammatory, and anti-microbial material. The third sensing material volume 160c can be a polymer, such as polypyrrole or polyaniline, Additionally or alternatively, the third sensing material volume can include molecules that facilitate analyte detection. In variations, the sensing layer can include one or more amine-decorated polymer materials. For instance, in examples, the amine-decorated polymer material(s) implemented can include one or more of: tyramine, phenylenediamine, lysine, and any other suitable amine-decorated polymer.

Preferably, as shown in FIG. 11B, the third sensing material volume 160c is directly coupled to portions of the third conductive layer 140c exposed through the other layers (e.g., the third isolating layer 150b). In a specific example, wherein the third conductive layer 140c forms a sheath (or tube) about the third isolating layer 150c, the third sensing material volume can form a tube of material coupled to the exposed cylindrical surface of the third conductive layer 140c. However, the third sensing material layer 160c can alternatively cover any other suitable portion of the third conductive layer 140c, the substrate 130 and/or any other suitable layer of the multi-electrode sensor 300.

Figure 12A:
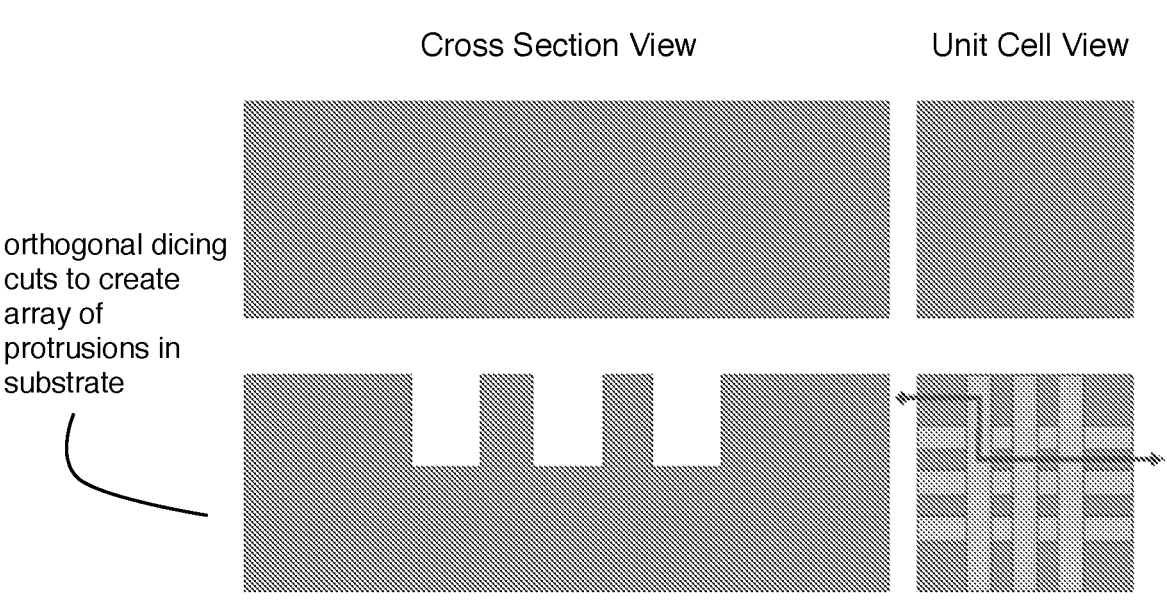
FIGS. 12A-12E depict portions of an embodiment of a method for manufacturing of a multi-electrode microsensor for biomonitoring.
Figure 12B:
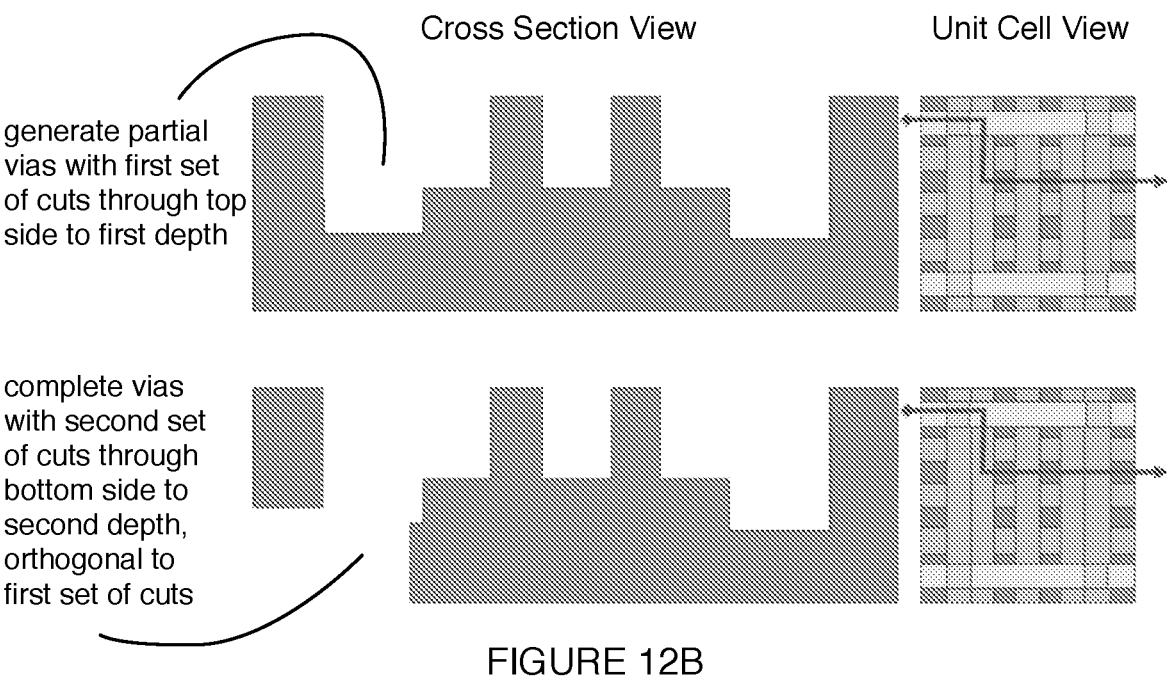

As in Section 1 above, any additional layers (e.g., selective layers analogous to the selective coating 170 described above, adhesion layers analogous to the adhesion coating 180 described above, functional layers analogous to the functional layer 190 described above, etc.) can be included in the multi-electrode sensor 2.5.2 Multi-Electrode Probe Manufacturing In a first example of manufacturing a multi-electrode probe array, as shown in FIG. 12A, an array of columnar protrusions can be formed as in Block S211b, for multiple units of the sensor, by removing material of the substrate (e.g., highly doped single crystal silicon) with a dicing saw to a first depth, using two series of dicing cuts at a first side of the substrate, wherein in the first series of dicing cuts, the saw is passed orthogonal to the trajectory of the saw during the second series of dicing cuts. However, in variation of this example, the first series of dicing cuts may not be orthogonal to the second series of dicing cuts (e.g., the two series may be angled relative to each other, but not orthogonal). In this example, as shown in FIG. 10B, the edges of each unit of the sensor can be left uncut, where separation of adjacent units occurs after further bulk processing of the units simultaneously, as described in Block S260 above. Then, in this example, as shown in FIG. 12B, a set of cuts to a second depth (deeper than the first depth) can be made across the first side of the substrate, thereby forming a partial via at each side of each sensor unit, at the first side of the substrate. Then, as shown in FIG. 12B, the partial via can be completed by cutting along a path orthogonal to the path for formation of the partial vias, at a second side of the substrate opposing the first side of the substrate, wherein the depth of cutting at the second side of the substrate is intermediate that of the first depth and the second depth of cutting at the first side of the substrate. Thus, vias can be formed that provide conductive pathways through the thickness of the substrate, such that conducting regions of the sensor units can be coupled to an electronics subsystem for signal reception and/or processing.

Figure 12C:
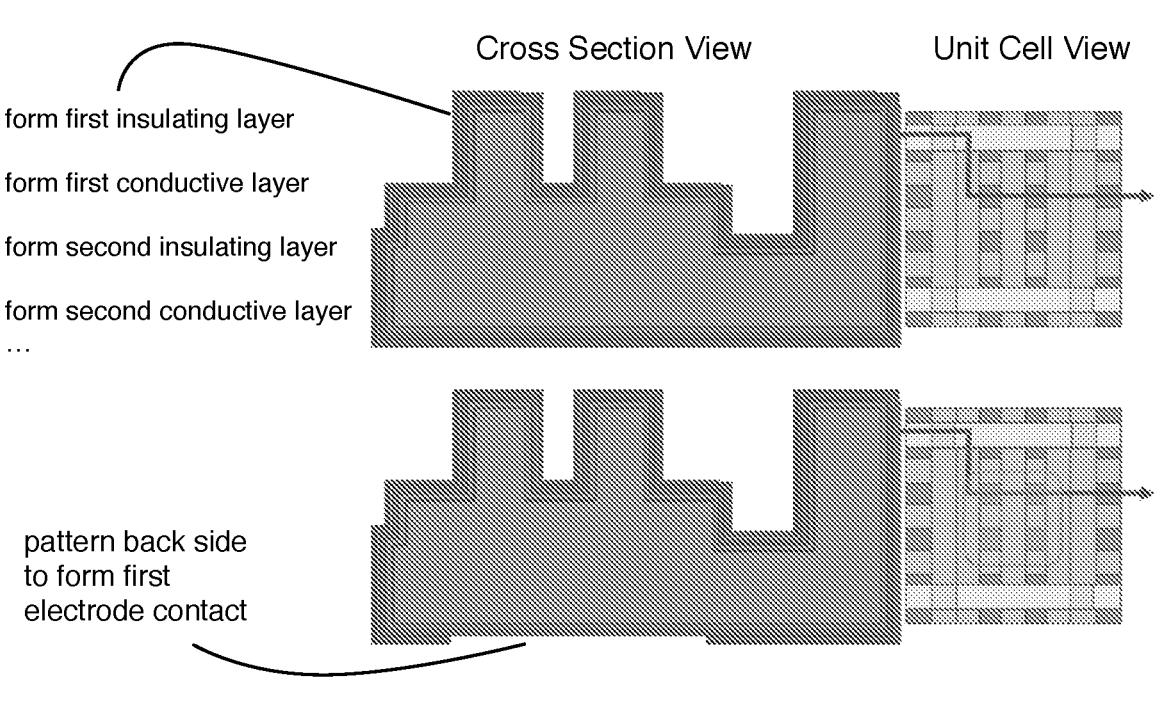

In this example, as shown in FIG. 12C, a first insulating layer can then be deposited at exposed surfaces of the substrate (in a manner analogous to Block S230 above, wherein in a specific example the insulating layer includes 2 μm oxide), a first conductive layer (e.g., 3 μm of in-situ doped poly-silicon) can be deposited over the first insulating layer in a manner analogous to Block S220, a second insulating layer can be deposited over the first conductive layer (in a manner analogous to Block S230 above, wherein in a specific example the insulating layer includes 2 μm oxide), and a second conductive layer (e.g., 3 μm of in-situ doped poly-silicon) can be deposited over the second insulating layer in a manner analogous to Block S220. As shown in FIG. 12C, Following deposition of the insulating and conductive layers, a first electrode contact (e.g., outer electrode contact) can be formed by patterning/etching the respective conductive layers and insulating layers associated with the first electrode of the multi-electrode probe. Alternatively, the electrode contact(s) can be formed at an earlier stage (e.g., prior to controlled deposition of insulating layers). Then, as shown in FIG. 11D, a second electrode contact (e.g., outer electrode contact) and a probe electrode contact can be formed by patterning/etching the respective conductive layers and insulating layers associated with the second electrode and probe electrode of the multi-electrode probe.

Figure 12D:
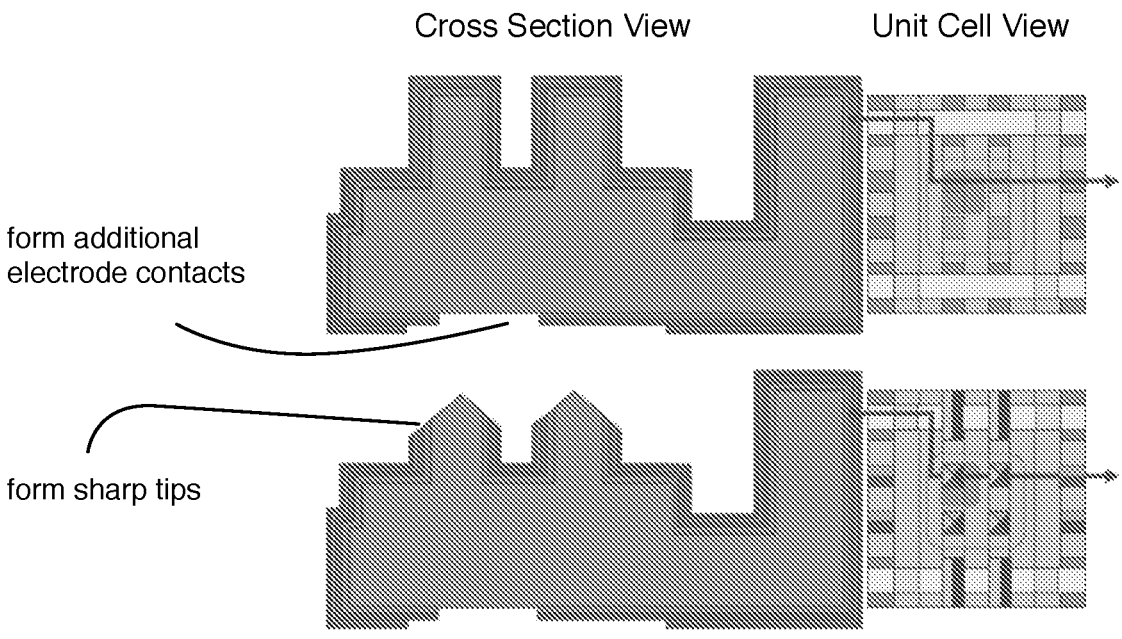

Then, as shown in FIG. 12D, an angled blade of a dicing saw can be passed across the array of columnar protrusions a desired number of times and/or with a desired number of orientations to produce the array of sharp protrusions, wherein the substrate material is exposed at the tip regions of the sharp protrusions through the insulating and conductive layers. After forming the array of sharp protrusions, the example method can additionally or alternatively include cleaning an/or removing artifacts (e.g., stringers) using an acid dip (e.g., hydrofluoric acid dip, hydrofluoric nitric acetic acid dip, etc.).

Figure 12E:
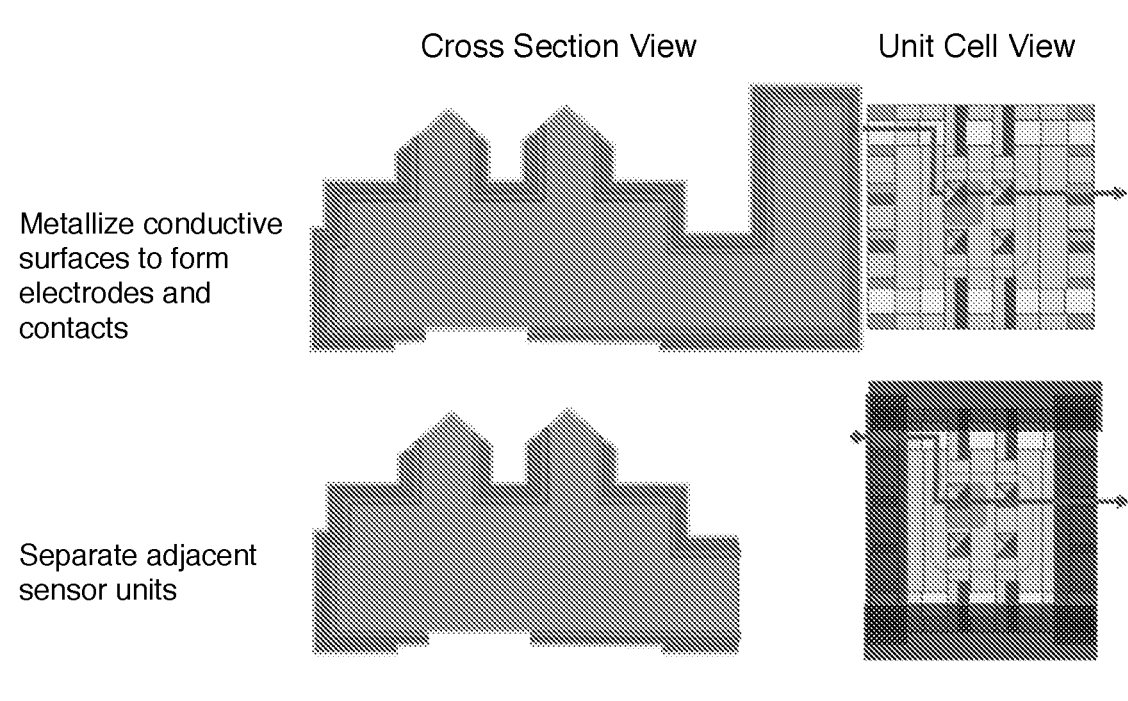

Then, as shown in FIG. 12E, all exposed conductive surfaces of the sensor units can be metallized, in order to form electrodes and contacts simultaneously. Alternatively, as described in relation to Block S270 above, metallization can occur in multiple stages, in relation to other steps of fabrication. After metallization, adjacent sensor units can be separated as in Block S260, wherein in the example, the second side of the assembly (e.g., back side of the wafer substrate) is taped, and adjacent units are separated by dicing at the first side (i.e., front side) of the substrate.

Variations of the example method above can be performed in any other suitable manner to generate a multi-electrode probe array. For instance, in relation to generation of vias through the substrate (e.g., a variation of the methods shown in FIG. 12B), a substrate (e.g., highly doped single crystal silicon) can be processed, as shown in FIG. 13A with a protective layer in a manner analogous to Block S258 described above, wherein in the specific example, the protective layer is either a) grown using a tetramethylammonium hydroxide (TMAH) process to generate an oxide layer (e.g., 2 μm thick), or b) grown using a potassium hydroxide (KOH) process to generate an oxide layer (e.g., 1000 Å thick), after which, a deposition process (e.g., a chemical vapor deposition process, a liquid plasma chemical vapor deposition process, etc.) is used to deposit a stoichiometric nitride layer (e.g., over the oxide layer, 5000 Å thick).

Then, as shown in FIG. 13B, a first side of the substrate, processed with the protective layer, can be patterned and etched to remove material of the protective layer in a first pattern, wherein in the specific example, the first pattern includes a contiguous and substantially large region (e.g., large square region) of the first side of the substrate. Then, a second side of the substrate opposing the first side of the substrate and processed with the protective layer, can be patterned and etched to remove material of the protective layer in a second pattern, wherein the second pattern is preferably aligned with the first pattern and mirrors the first pattern across the thickness of the substrate. However, in variations of the example, the first and the second patterns may not be aligned and/or may not mirror each other across the thickness of the substrate.

Figure 13C:
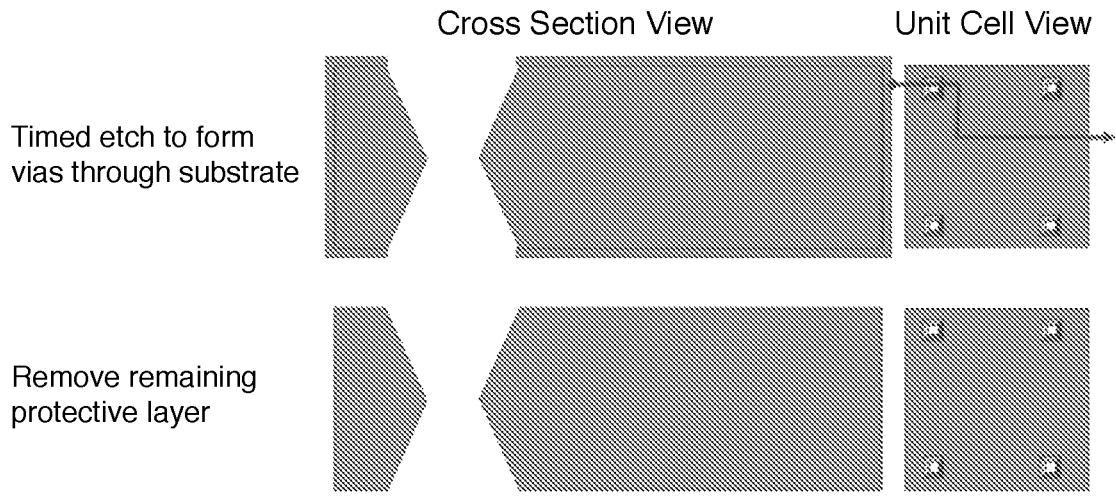

Next, as shown in FIG. 13C, both the first side and the second side of the substrate, exposed through the protective layer by the first pattern and the second pattern, can be etched (e.g., contemporaneously, simultaneously, non-contemporaneously, in stages, etc.) to generate vias that connect the first side of the substrate to the second side of the substrate, in order to provide conduction pathways for units of the sensor. In this step of the example, etching can be performed using a KOH process, a TMAH process, and/or any other suitable etching process. The process used at the first side of the substrate can be identical to the process used at the second side of the substrate; however, the etching processes used at the sides of the substrate can alternatively be different. Finally, as shown in FIG. 13C, the protective layer can be removed using an acid wash process (e.g., a hydrofluoric acid process) for oxide removal and/or an acid wash process (e.g., a phosphoric acid process) for nitrides. However, the vias can be generated in any other suitable manner.

Variations of the example methods above can include formation of any suitable number of electrodes. Furthermore, variations of the example method above can additionally or alternatively include any one or more of: passivation of metallized surfaces (e.g., to prevent shorting of electrode units, etc.);

The method 200 can additionally or alternatively include any other suitable Blocks or Steps configured to generate an array of filaments for analyte sensing during contact with a body fluid of the user. As such, the method 200 can include any one or more of: coupling an adhesion layer to any suitable layer used during the method, wherein the adhesion layer functions to facilitate maintenance of coupling of the layer(s) for robustness; coupling a temporary functional layer to the selective layer, which facilitates penetration into the body of the user and/or calibration of the microsensor; providing a functional external layer configured to suppress or prevent an inflammatory response (e.g., by comprising a surface treatment or an anti-inflammatory agent), prevent bio-rejection, prevent encapsulation (e.g., by comprising a bio-inert substance, such as pyrolytic carbon), enhance target analyte/ion detection, and/or provide any other suitable anti-failure mechanism; and processing the substrate according to any other suitable process.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A wearable sensor for sensing analytes, the wearable sensor comprising:
    an analyte microsensor including a plurality of microneedles configured to detect at least one analyte in interstitial fluid in skin of a user, wherein at least one individual microneedle in the plurality of microneedles includes:
    a distal region;
    an active region isolated to the distal region, the active region including a sensing material operable to generate analyte signals upon detection of the at least one analyte and a conductive material isolated to the distal region;
    a base region; and
    a needle body with an insulating material extending between the base region and the distal region to electrically insulate the needle body of the at least one individual microneedle;
    an electronics module electrically coupled to the base region and programmed to receive output from the analyte microsensor and to determine analyte information about the at least one analyte based on the received output.

2. The wearable sensor of claim 1, herein the needle body is a columnar protrusion, wherein the electronics module electrically coupled to the analyte microsensor via a substrate, and the received output includes the generated analyte signals.

3. The wearable sensor of claim 1, wherein:
the conductive material of the at least one individual microneedle is operable to transmit the generated analyte signals; and
the at least one individual microneedle further includes:
   a non-active region extending proximally from the active region to the base region, wherein the non-active region includes the insulating material that electrically insulates a portion of the at least one individual microneedle configured to transmit the generated analyte signals.

4. The wearable sensor of claim 1, wherein the distal region is a sharp tip configured to penetrate the user's skin.

5. The wearable sensor of claim 1, wherein:
the analyte microsensor is configured to detect first and second analytes;
the analyte microsensor is configured to output signals associated with detection of the first and second analytes .

6. The wearable sensor of claim 1, wherein the sensing material is one of a plurality of two or more functionally distinct layers that cooperate to detect the at least one analyte.

7. The wearable sensor of claim 6, wherein the plurality of two or more functionally distinct layers includes at least one of an intermediate active layer, an intermediate selective layer, or a stabilizing layer.

8. The wearable sensor of claim 6, wherein the plurality of two or more functionally distinct layers includes a layer of enzymes configured to catalyze a reaction with the at least one analyte to produce a mediator species.

9. The wearable sensor of claim 1, wherein each of the plurality of microneedles has a columnar protrusion ensheathed by the insulating material.

10. The wearable sensor of claim 1, wherein the active region is isolated to a piercing tip of the at least one individual microneedle.

11. A wearable sensor for sensing analytes, the wearable sensor comprising:
   an analyte microsensor including a plurality of microneedles configured to detect at least one analyte in interstitial fluid of a user, wherein each individual microneedle includes a base region, a distal region, and a non-active needle body, wherein the distal region has:
   a sensing material configured to generate analyte signals upon detection of the at least one analyte;
   a conductive portion isolated to the distal region and configured to transmit the generated analyte signals; and
the non-active needle body extends between the base region and the distal region, wherein the non-active needle body includes an insulating material covering all of an exterior portion of the non-active needle body extending between the distal region and the base region.

12. The wearable sensor of claim 11, wherein the wearable sensor is configured to determine a concentration of the at least one analyte based on the generated analyte signals.

13. The wearable sensor of claim 11, wherein the sensing material is one of a plurality of two or more functionally distinct layers that cooperate to detect the at least one analyte, and wherein the plurality of two or more functionally distinct layers includes at least one of an intermediate active layer, an intermediate selective layer, or a stabilizing layer.

14. The wearable sensor of claim 11, wherein the plurality of microneedles includes
   a first set of first microneedles configured to detect a first analyte, and
   a second set of microneedles configured to detect a second analyte different from the first analyte.

15. The wearable sensor of claim 11, wherein
the sensing material forms a sensing layer, a conductive material forms the conductive portion, the insulating material forms an insulating layer.

16. The wearable sensor of claim 11, wherein the wearable sensor includes a chip and circuitry integrated into the chip to process analyte detection signals based on the detected at least one analyte.

17. The wearable sensor of claim 11, wherein the at least one analyte is a single analyte.

18. The wearable sensor of claim 11, wherein the at least one analyte is a plurality of analytes.

* * * * *